US012714709B2

(12) United States Patent
Buschmann et al.

(10) Patent No.: US 12,714,709 B2
(45) Date of Patent: Aug. 25, 2026

(54) PHARMACEUTICAL COMPOSITIONS COMPRISING 2-[(4S)-8-FLUORO-2-[4-(3-METHOXYPHENYL)PIPERAZIN-1-YL]-3-[2-METHOXY-5-(TRIFLUOROMETHYL)PHENYL]-4H-QUINAZOLIN-4-YL]ACETATE AND SODIUM IONS

(71) Applicant: AIC246 AG & Co. KG, Wuppertal (DE)

(72) Inventors: Helmut Buschmann, Aachen (DE); Thomas Goldner, Velbert (DE); Jessica Redmer, Monchengladbach (DE); Jordi Carles Ceron Bertran, La Pobla de Montornes (ES); Andrea Hawe, Munich (DE); Matthias Lucke, Munich (DE); Dorothea Hohmann, Hamburg (DE); Monica Rosa, Munich (DE)

(73) Assignee: AIC246 AG & Co. KG, Wuppertal (DE)

( * ) Notice: Subject to any disclaimer, the term of this patent is extended or adjusted under 35 U.S.C. 154(b) by 814 days.

(21) Appl. No.: 17/802,558

(22) PCT Filed: Mar. 1, 2021

(86) PCT No.: PCT/EP2021/055057

§ 371 (c)(1),
(2) Date: Aug. 26, 2022

(87) PCT Pub. No.: WO2021/170875

PCT Pub. Date: Sep. 2, 2021

(65) Prior Publication Data

US 2023/0138444 A1 May 4, 2023

(30) Foreign Application Priority Data

Feb. 27, 2020 (EP) .................................... 20159711

(51) Int. Cl.

| | |
|---|---|
| ***A61K 31/517*** | (2006.01) |
| ***A61K 9/00*** | (2006.01) |
| ***A61K 9/08*** | (2006.01) |
| ***A61K 9/10*** | (2006.01) |
| ***A61K 9/19*** | (2006.01) |
| ***A61K 47/10*** | (2017.01) |
| ***A61K 47/18*** | (2017.01) |
| ***A61K 47/26*** | (2006.01) |
| ***A61K 47/32*** | (2006.01) |
| ***A61K 47/40*** | (2006.01) |
| ***A61P 31/20*** | (2006.01) |
| ***A61P 31/22*** | (2006.01) |

(52) U.S. Cl.

CPC .............. *A61K 31/517* (2013.01); *A61K 9/19* (2013.01); *A61K 47/10* (2013.01); *A61K 47/18* (2013.01); *A61K 47/26* (2013.01); *A61K 47/32* (2013.01)

(58) Field of Classification Search

CPC ........ A61K 31/517; A61K 9/19; A61K 47/10; A61K 47/18; A61K 47/26; A61K 47/32; A61K 9/0019; A61K 9/08; A61K 9/10; A61K 47/183; A61K 47/40; A61P 31/22; A61P 31/20

See application file for complete search history.

(56) References Cited

U.S. PATENT DOCUMENTS

| | | | | |
|---|---|---|---|---|
| 8,513,255 | B2 | 8/2013 | Wunberg et al. | |
| 9,637,459 | B2 * | 5/2017 | Grunenberg ............ | A61P 31/00 |
| 10,603,384 | B2 | 3/2020 | Paulus et al. | |
| 2015/0038514 | A1 | 2/2015 | Grunenberg et al. | |
| 2016/0346287 | A1 | 12/2016 | Volinsky et al. | |
| 2023/0095980 | A1 | 3/2023 | Buschmann et al. | |
| 2023/0138444 | A1 | 5/2023 | Buschmann et al. | |
| 2023/0150950 | A1 | 5/2023 | Buschmann et al. | |
| 2023/0219899 | A1 | 7/2023 | Buschmann et al. | |
| 2023/0219900 | A1 | 7/2023 | Buschmann et al. | |

FOREIGN PATENT DOCUMENTS

| | | | |
|---|---|---|---|
| CL | 2022002290 | A1 | 2/2023 |
| CL | 2022002291 | A1 | 2/2023 |
| CL | 2022002292 | A1 | 2/2023 |
| CL | 2022002294 | A1 | 2/2023 |
| CN | 104144678 | A | 11/2014 |
| CN | 109966244 | A | 7/2019 |

(Continued)

OTHER PUBLICATIONS

Gupta et al. Salts of Therapeutic Agents: Chemical, Physicochemical, and Biological Considerations, Molecules,2018, 23, 1719 (Year: 2018).*

(Continued)

*Primary Examiner* — Bruck Kifle

*Assistant Examiner* — Kevin S Martin

(74) *Attorney, Agent, or Firm* — Millen, White, Zelano & Branigan, P.C.; Brion P. Heaney

(57) ABSTRACT

The present invention relates to new stable pharmaceutical compositions containing 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid and sodium ions that are essentially free from complexing solubilizing agents, such as PEG, cyclodextrin, lysine, arginine, in particular HPBCD. The invention further relates to methods of preparation of said pharmaceutical compositions. The invention further relates to use of said pharmaceutical compositions in methods of treatment of and/or as a prophylactic for illnesses, particularly its use as an antiviral, preferably against cytomegaloviruses.

24 Claims, No Drawings

(56) References Cited

FOREIGN PATENT DOCUMENTS

| | | | |
|---|---|---|---|
| JP | 2015508802 | A | 3/2015 |
| JP | 7590444 | B2 | 11/2024 |

OTHER PUBLICATIONS

Pubchem, Tromethamine, 2005: https://pubchem.ncbi.nlm.nih.gov/compound/Tromethamine (Year: 2005).*

Search report in corresponding EP 20159711.9 dated Aug. 31, 2020 (pp. 1-7).

International Search report PCT/EP2021/055057 dated Apr. 26, 2021 (pp. 1-4).

Tong et al: "Chapter 4—Salt Screening and Selection: New Challenges and Considerations in the Modern Pharmaceutical Research and Development Paradigm", Developing Solid Oral Dosage Forms, Pharmaceutical Theory And Practice, 2008, p. 78.

* cited by examiner

PHARMACEUTICAL COMPOSITIONS COMPRISING 2-[(4S)-8-FLUORO-2-[4-(3-METHOXYPHENYL)PIPERAZIN-1-YL]-3-[2-METHOXY-5-(TRIFLUOROMETHYL)PHENYL]-4H-QUINAZOLIN-4-YL]ACETATE AND SODIUM IONS

The present invention relates to new stable pharmaceutical compositions comprising 2-[(4S)-8-fluoro-2-[4-(3-methoxyphenyl)piperazin-1-yl]-3-[2-methoxy-5-(trifluoromethyl)phenyl]-4H-quinazolin-4-yl]acetatic acid, also known as letermovir, and sodium ions that are suitable for oral and intravenous application and for injection. Said pharmaceutical compositions are essentially free from particular complexing solubilizing agents, such as PEG, cyclodextrin, lysine, arginine, in particular HPBCD. Said formulations are suitable for use in methods of treatment of viral diseases, in particular human cytomegalovirus (hereinafter HCMV) infections. The invention also relates to methods of preparation of said pharmaceutical compositions.

BACKGROUND

Cytomegalovirus (CMV) is a common opportunistic infection that causes significant morbidity and preventable mortality after solid-organ and allogeneic hematopoietic stem cell transplantation.

HCMV is a species of virus that belongs to the viral family known as Herpesviridae or herpes viruses. It is typically abbreviated as HCMV and is alternatively known as human herpesvirus-5 (HHV-5). Within Herpesviridae, HCMV belongs to the Betaherpesvirinae subfamily, which also includes cytomegaloviruses from other mammals.

Letermovir is known as a highly active drug for addressing HCMV infection and extensively described in Lischka et al., *In Vitro and In Vivo Activities of the Novel Anticytomegalovirus Compound Letermovir. Antimicrob. Agents Chemother.* 2010, 54: p. 1290-1297, and Kaul et al., *First report of successful treatment of multidrug-resistant cytomegalovirus disease with the novel anti-CMV compound Letermovir. Am. J. Transplant.* 2011, 11:1079-1084; as well as Marschall et al., *In Vitro Evaluation of the Activities of the Novel Anticytomegalovirus Compound Letermovir against Herpesviruses and Other Human Pathogenic Viruses. Antimicrob. Agents Chemother.* 2012, 56:1135-1137.

The precise chemical name of letermovir is 2-[(4S)-8-fluoro-2-[4-(3-methoxyphenyl)-piperazin-1-yl]-3-[2-methoxy-5-(trifluoromethyl)phenyl]-4H-quinazolin-4-yl] acetic acid, and the chemical structure of letermovir is depicted below:

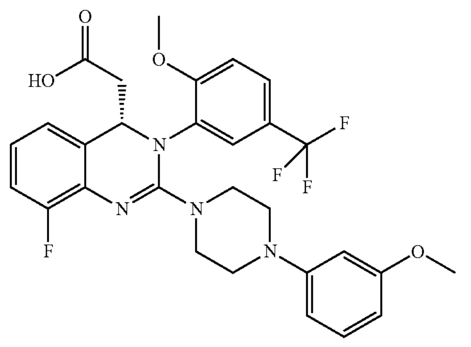 [SMILES: COc1cccc(N2CCN(C3=Nc4c(F)cccc4[C@H](CC(=O)O)N3c3cc(C(F)(F)F)ccc3OC)CC2)c1]

Letermovir was developed as an antiviral agent, in particular for the treatment, prevention, or prophylaxis of infections caused by the human cytomegalovirus (HCMV), and is disclosed in International Publication No. WO 2004/096778. In addition, salts of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid were also prepared, as described in International Publication No. WO 2013/127971.

Liquid pharmaceutical formulations comprising amorphous letermovir are described in International Publication No. WO 2013/127970 which relates to a pharmaceutical composition that can be used in particular for intravenous administration that contains letermovir, that has long-term stability and can be stored, and that in addition has a substantially physiological pH. It has further been discovered that such compositions can be lyophilized in order to obtain a stable, solid pharmaceutical composition that can be reconstituted in a simple manner for injection purposes, e.g. by adding water, as a result of which, in turn, a stable pharmaceutical composition, e.g. for intravenous administration, can be obtained.

There remains a need, however, for pharmaceutical compositions comprising letermovir having long-term stability at substantially physiological pH, that are suitable for use in subjects of all ages in the need of solid-organ transplantation and allogenic hematopoietic stem cell transplantation.

DESCRIPTION OF THE INVENTION

In a first aspect, the present invention relates to a pharmaceutical composition comprising letermovir of formula (I), and sodium ions (I)

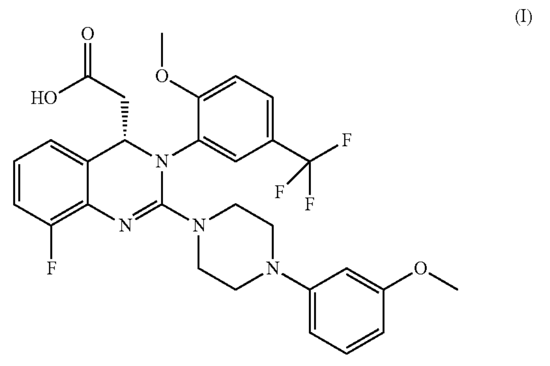 [SMILES: COc1cccc(N2CCN(C3=Nc4c(F)cccc4[C@H](CC(=O)O)N3c3cc(C(F)(F)F)ccc3OC)CC2)c1]

wherein the pharmaceutical composition comprises the sodium ions in a molar ratio to letermovir in the range of from 0.50 to <1.00:1.00, preferably of from 0.65 to <1.00:1.00, more preferably of from 0.72 to <1.00:1.00, more preferably of from 0.80 to <1.00:1.00, more preferably of from 0.80 to 0.90:1.00; and is capable of exhibiting a pH in the range of from 7 to 8, when said pharmaceutical composition is dissolved in water in a concentration range of from 1 to 100 mg/mL with respect to letermovir; and is essentially free from complexing solubilizing agents selected from the group consisting of PEG, lysine, arginine, a cyclodextrin, in particular a hydroxypropyl-beta-cyclodextrin (HPBCD).

With the molar ratio of the sodium ions to letermovir in the range of from 0.50 to <1.00:1.00, preferably of from 0.65 to <1.00:1.00, more preferably of from 0.72 to <1.00:1.00, more preferably of from 0.80 to <1.00:1.00, more preferably of from 0.80 to 0.90:1.00, letermovir exhibits an improved solubility and is present in a concentration sufficient to achieve the desired therapeutic effect without the need to use any further solubilizers, in particular complexing solubilizing agents such as cyclodextrins. In addition, the pharmaceutical composition which comprises the sodium ions in said ratio, has a substantially physiological pH and exhibits long-term stability.

It has been further discovered that said pharmaceutical composition can be obtained in a form of a lyophilizate that can be fully reconstituted in a parenterally acceptable diluent, such as water, glucose aqueous solution or Ringer's lactate solution. When reconstituted, said lyophilizate exhibits a pH in the range of from 7 to 8, preferably from 7.4 to 7.8, if Letermovir is present in a concentration range of from 1 to 100 mg/mL, preferably of from 20 to 100 mg/mL in said reconstituted solution. The pH of said reconstituted solution remains stable with molar ratio of the sodium ions to letermovir in the range of from 0.50 to <1.00:1.00, preferably of from 0.65 to <1.00:1.00, more preferably of from 0.72 to <1.00:1.00, more preferably of from 0.80 to <1.00:1.00, more preferably of from 0.80 to 0.90:1.00, and is in the physiological range of from 7 to 8, preferably of from 7.4 to 7.8, what is a clear evidence of a surprising self-buffering effect of the sodium ions in the given ranges. The obtained reconstituted solutions exhibit a long-term stability.

In another aspect, the present invention relates to a method of producing of said pharmaceutical compositions, comprising the following steps:

i) providing a solution of letermovir and sodium ions, wherein the molar ratio of sodium ions to letermovir is in the range of from 0.50 to <1.00:1.00, preferably of from 0.65 to <1.00:1.00, more preferably of from 0.72 to <1.00:1.00, more preferably of from 0.80 to <1.00:1.00, more preferably of from 0.80 to 0.90:1.00, in particular of from 0.84 to 0.88:1.00; and optionally at least one excipient selected from the group consisting of a carbohydrate, in particular sucrose or mannitol, an amino acid, in particular phenylalanine, a polyalkoxy compound, in particular a poloxamer, more particular poloxamer 188, and a polyvinylpyrrolidone (PVP), in particular PVP PF12;
ii) if needed adjusting the pH of the solution obtained in step i) to a range of from 7 to 8 preferably with HCl;
iii) optionally filtering said solution.

In particular, the method according to the invention may further comprise the subsequent steps of freeze-drying the solution obtained in step iii above, to provide a lyophilizate and optionally reconstituting the lyophilizate in a first parenterally acceptable diluent to provide a reconstituted solution in a concentration range of from 1 to 100 mg/mL, preferably 20 to 100 mg/mL, with respect to letermovir and optionally further diluting said reconstituted solution with a second parenterally acceptable diluent to a final concentration which is acceptable for injection or infusion, and wherein said first and said second parenterally acceptable diluents can be the same or different.

Another aspect of the present invention relates to the use of the pharmaceutical compositions described herein for the preparation of a medicament for the treatment and/or prevention of diseases, in particular of viral infections, preferably human cytomegalovirus (HCMV) infections or infections with another member of the herpes viridae group.

Another aspect of the present invention relates to a method of the treatment and/or prevention virus infections, preferably human cytomegalovirus (HCMV) infections or infections with another member of the herpes viridae group, in a subject in need thereof by administering said pharmaceutical compositions. In particular, the pharmaceutical compositions according to the present invention are suitable for treatment of neonates, subjects in the need of particular solid-organ transplantation, e.g. subjects with kidney damages and subjects in need of allogenic hematopoietic stem cell transplantation.

DETAILED DESCRIPTION

It is noted that the term "comprising" also encompasses the meaning "consisting of", e.g., a group of members comprising said members also encompasses a group of members consisting only of these members.

The term "room temperature" as used herein, is synonymous to the term "standard room temperature" and refers to a temperature in the range of from 19° C. to 26° C. For example, "stirring at room temperature" means "stirring at a temperature in the range of from 19° C. to 26° C.".

Within the scope of the invention the term "stability" is understood to mean not only the chemical stability of the constituents of the pharmaceutical composition, in particular, the active substance, but also the physicochemical stability of the composition itself. In particular, the composition according to the invention must be stable against precipitation of the constituents.

In this context, the term "stability" means that at 2° C. to 8° C., or at 25° C. or at 40° C. the pharmaceutical compositions according to the invention contain a minimum proportion of >90%, preferably >95%, and more preferably >98% of the active substance for a storage period of at least one month, preferably at least three months, even more preferably at least 6 months, even more preferably 12 months, even more preferably 18 months, and most preferred at least 36 months, when said liquid pharmaceutical compositions are measured according to the HPLC method of the present invention.

A cyclodextrin according to the invention is understood to be any modified or non-modified cyclodextrin, in particular selected from α-cyclodextrins, β-cyclodextrins or γ-cyclodextrins. The examples of modified β-cyclodextrins include, in particular, hydroxyalkyl-β-cyclodextrins, e.g. hydroxymethyl-β-cyclodextrins, hydroxyethyl-β-cyclodextrins or hydroxypropyl-β-cyclodextrins, alkyl-hydroxyalkyl-β-cyclodextrins, e.g. methyl-hydroxypropyl-β-cyclodextrins or ethyl-hydroxypropyl-cyclodextrins or sulfoalkyl-cyclodextrins. Hydroxypropyl-β-cyclodextrins are available in various degrees of substitution, in particular 2-hydroxypropyl-β-cyclodextrin is available as Cavasol® W7 HP, Cavitron® W7 HP5 and Cavitron® W7 HP7.

As used herein the term "complexing solubilizing agents" refers to the compounds which enhance solubility of the active ingredient of the pharmaceutical composition of the invention by forming coordination bonds between said compound and the molecule of the active ingredient, in particular in an aqueous solution, i.e. by actually and detectably forming a complex with the active ingredient of the pharmaceutical composition of the invention. The non-limiting examples of complexing solubilizing agents include non-polymeric solubilizers, such as lysine or arginine, and polymeric solubilizers, such as PEG or cyclodextrins.

As used herein the term "parenterally acceptable diluents", "parenteral admixture diluents" and "commercial diluents" refer to any liquid material which is used to dilute an active ingredient, which is suitable for administration to a subject by a route other than topical or oral. Examples of parenteral routes include intramuscular, intravascular (including intraarterial or intravenous), intraorbital, retrobulbar, intranasal, intrathecal, intraventricular, intraspinal, intraperitoneal, intrapulmonary, intracisternal, intracapsular, intrasternal, peribulbar, or intralesional administration. Examples of parenterally acceptable diluents include water, glucose aqueous solution or Ringer's lactate solution. Within the application the terms "commercial diluents", "parenteral admixture diluents" and „parenterally acceptable diluents" have the same meaning and are used interchangeably.

As used herein, the term "carbohydrate" refers to compounds that are polyhydroxy aldehydes or ketones, or substances that yield such compounds on hydrolysis. Some carbohydrates may further contain nitrogen, phosphorous, or sulfur. Examples of carbohydrates include monosaccharides, disaccharides, oligosaccharides, and polysaccharides, in particular sucrose and mannitol.

As used herein, the term "amino acid" refers to any of the twenty naturally occurring amino acids or their synthetic analogs with unnatural side chains and including both D and L optical isomers. The examples of amino acids include, in particular, alanine and phenylalanine.

As used herein, the term "polyalkoxy compounds" refers to the polymeric compounds in which the repeating units represent alkyl groups having straight or brached chain linked to an oxygen atom. The examples of polyalkoxy compounds include poloxamers, in particular, poloxamer 188.

Within the scope of the present invention the terms "obtained by" and "obtainable by" have the same meaning and are used interchangeably.

Within the scope of the present invention the term "equivalents" is understood to mean "molar equivalents".

As used herein the term "aqueous solution" refers to liquid homogeneous mixtures comprising water.

As used herein, the terms "lyophilization" and "freeze-drying" are used interchangeably and mean a process by which a desired product containing a solvent, in particular water, is cooled to a sufficient temperature, in particular by using liquid nitrogen or cooled shelves, at which a portion or all of the solvent is frozen and the frozen solvent is further removed by one or more drying steps, in particular by removal of unbound solvent by sublimation and desorption. The terms "lyophilizate" and "freeze-dried product" refer to the product obtained by freeze-drying and are used interchangeably throughout the application.

As used herein, the term "reconstitution" or "reconstituting" refers to a process of dissolving a lyophilizate in a diluent, preferably in a parenterally acceptable diluent, in particular water. The term "reconstituted solution" refers to the product obtained by reconstitution.

As used herein the term "treatment" or "treating" is defined as the application or administration of a therapeutic agent i.e., letermovir (alone or in combination with another pharmaceutical agent) to a subject, or application or administration of a therapeutic agent to an isolated tissue or cell line from a subject who has an HCMV infection, a symptom of HCMV infection, or the potential to develop an HCMV infection with the purpose to cure, heal, alleviate, relieve, alter, remedy, ameliorate, improve or affect the HCMV infection, the symptoms of HCMV infection or the potential to develop an HCMV infection. Such treatments may be specifically tailored or modified based on knowledge obtained from the field of pharmacogenomics.

As used herein the term "prevent", "preventing" or "prevention" means no disorder or disease development if none had occurred, or no further disorder or disease development if there had already been development of the disorder or disease. Also considered is the ability of one to prevent some or all of the symptoms associated with the disorder or disease. Prevention of diseases encompasses prophylaxis of diseases.

As used herein the term "subject" refers to a human or a non-human mammal. Non-human mammals include for example livestock and pets such as ovine, bovine, porcine, feline, canines and murine mammals. Preferably the subject is human. In one embodiment, the subject is a human infant. In a preferred embodiment, the subject is a human neonate. In another preferred embodiment, the subject is a subject in the need of particular solid-organ transplantation, e.g. a subject with kidney damages and a subject in need of allogenic hematopoietic stem cell transplantation.

As used herein the term "pharmaceutically acceptable" refers to a material such as a carrier or diluent which does not abrogate the biological activity or properties of the compound and is relatively non-toxic i.e. the material may be administered to a subject without causing undesirable biological effects or interacting in a deleterious manner with any of the components of the composition in which it is contained.

As used herein the term "essentially free" refers to a content of less than 5 mole %.

The subject-matter of the present invention relates to a pharmaceutical composition comprising letermovir of formula (I), and sodium ions (I)

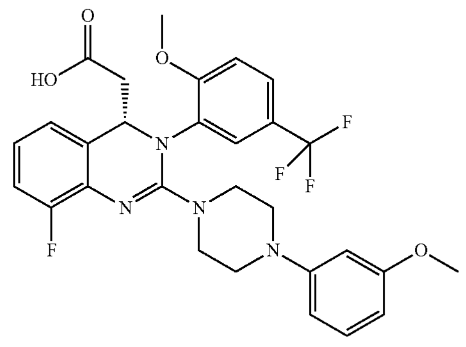

wherein the pharmaceutical composition comprises the sodium ions in a molar ratio to letermovir in the range of from 0.50 to <1.00:1.00, preferably of from 0.65 to <1.00:1.00, more preferably of from 0.72 to <1.00:1.00, more preferably of from 0.80 to <1.00:1.00, more preferably of from 0.80 to 0.90:1.00; and is capable of exhibiting a pH in the range of from 7 to 8, preferably from 7.4 to 7.8, when said pharmaceutical composition is dissolved in water in a concentration range of from 1 to 100 mg/mL, preferably 20 to 100 mg/mL, with respect to letermovir; and is essentially free from complexing solubilizing agents selected from the group consisting of PEG, lysine, arginine, a cyclodextrin, in particular a hydroxypropyl-beta-cyclodextrin (HPBCD).

The subject-matter of the present invention further relates to a pharmaceutical composition comprising letermovir of formula (I), and sodium ions (I)

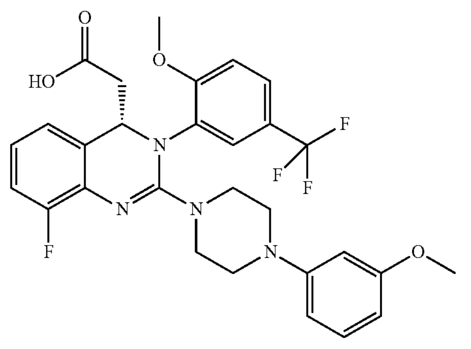

wherein the pharmaceutical composition comprises the sodium ions in a molar ratio to letermovir in the range of from 0.80 to <1.00:1.00, preferably of from 0.80 to 0.90:1.00; and is capable of exhibiting a pH in the range of from 7 to 8, preferably from 7.4 to 7.8, when said pharmaceutical composition is dissolved in a glucose aqueous solution, preferably 5% w/v glucose solution in water, in a concentration range of from 1 to 100 mg/mL, preferably 20 to 100 mg/mL, with respect to letermovir; and is essentially free from complexing solubilizing agents selected from the group consisting of PEG, lysine, arginine, a cyclodextrin, in particular a hydroxypropyl-beta-cyclodextrin (HPBCD).

The subject-matter of the present invention further relates to a pharmaceutical composition comprising letermovir of formula (I), and sodium ions (I)

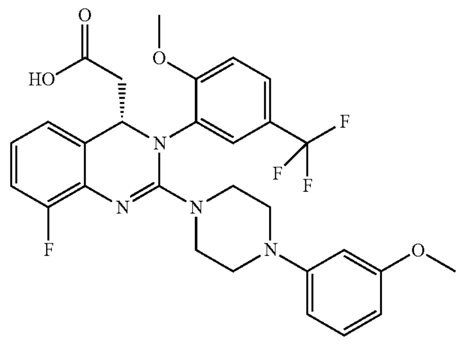

wherein the pharmaceutical composition comprises the sodium ions in a molar ratio to letermovir in the range of from 0.64 to <1.00:1.00, preferably of from 0.72 to <1.00:1.00, more preferably of from 0.80 to <1.00:1.00, more preferably of from 0.80 to 0.90:1.00; and is capable of exhibiting a pH in the range of from 7 to 8, preferably from 7.4 to 7.8, when said pharmaceutical composition is dissolved in Ringer's lactate solution in a concentration range of from 1 to 100 mg/mL, preferably 20 to 100 mg/mL, with respect to letermovir; and is essentially free from complexing solubilizing agents selected from the group consisting of PEG, lysine, arginine, a cyclodextrin, in particular a hydroxypropyl-beta-cyclodextrin (HPBCD).

In one embodiment, a pharmaceutical composition according to the invention is essentially free from a compound selected from the group consisting of PEG, lysine, arginine, and a cyclodextrin. In one embodiment a pharmaceutical composition according to the invention is essentially free from lysine. In another embodiment a pharmaceutical composition according to the invention is essentially free from arginine. In yet another embodiment a pharmaceutical composition according to the invention is essentially free from PEG. In yet another embodiment a pharmaceutical composition according to the invention is essentially free from a cyclodextrin. In a preferred embodiment a pharmaceutical composition according to the invention is essentially free from hydroxypropyl-beta-cyclodextrin. In another preferred embodiment a pharmaceutical composition according to the invention is essentially free from PEG, lysine, arginine and a cyclodextrin, in particular a hydroxypropyl-beta-cyclodextrin (HPBCD).

In one embodiment a pharmaceutical composition according to the invention is essentially free from complexing solubilizing agents, in particular essentially free from PEG, lysine, arginine, and a cyclodextrin, in particular a hydroxypropyl-beta-cyclodextrin (HPBCD).

In one embodiment, the content of complexing solubilizing agents in a pharmaceutical composition according to the invention is less than 5 mole %. In a preferred embodiment, the content of complexing solubilizing agents in a pharmaceutical composition according to the invention is less than 3 mole %. In a more embodiment, the content of complexing solubilizing agents in a pharmaceutical composition according to the invention is less than 1 mole %. In a more preferred embodiment, the content of complexing solubilizing agents in a pharmaceutical composition according to the invention is less than 0.5 mole %. Most preferred, the content of complexing solubilizing agents in a pharmaceutical composition according to the invention is less than 0.3 mole %.

In one embodiment the pharmaceutical composition according to the present invention comprises letermovir and sodium ions, wherein said pharmaceutical composition:

comprises the sodium ions in a molar ratio to letermovir in the range of from 0.50 to <1.00:1.00; and is capable of exhibiting a pH in the range of from 7 to 8, preferably from 7.4 to 7.8, when said pharmaceutical composition is dissolved in water in a concentration range of from 1 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

comprises the sodium ions in a molar ratio to letermovir in the range of from 0.80 to <1.00:1.00; and is capable of exhibiting a pH in the range of from 7 to 8, preferably from 7.4 to 7.8, when said pharmaceutical composition is dissolved in water in a concentration range of from 1 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In a preferred embodiment the pharmaceutical composition according to the present invention comprises letermovir and sodium ions, wherein said pharmaceutical composition:

- comprises the sodium ions in a molar ratio to letermovir in the range of from 0.80 to 0.90:1.00; and
- is capable of exhibiting a pH in the range of from 7 to 8, preferably from 7.4 to 7.8, when said pharmaceutical composition is dissolved in water in a concentration range of from 1 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In a more preferred embodiment the pharmaceutical composition according to the present invention comprises letermovir and sodium ions, wherein said pharmaceutical composition:

- comprises the sodium ions in a molar ratio to letermovir in the range of from 0.84 to 0.88:1.00; and
- is capable of exhibiting a pH in the range of from 7 to 8, preferably from 7.4 to 7.8, when said pharmaceutical composition is dissolved in water in a concentration range of from 1 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

- comprises the sodium ions in a molar ratio to letermovir in the range of from 0.50 to <1.00:1.00; and
- is capable of exhibiting a pH in the range of from 7 to 8, preferably from 7.4 to 7.8, when said pharmaceutical composition is dissolved in water in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

- comprises the sodium ions in a molar ratio to letermovir in the range of from 0.80 to <1.00:1.00; and
- is capable of exhibiting a pH in the range of from 7 to 8, preferably from 7.4 to 7.8, when said pharmaceutical composition is dissolved in water in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In a preferred embodiment the pharmaceutical composition according to the present invention comprises letermovir and sodium ions, wherein said pharmaceutical composition:

- comprises the sodium ions in a molar ratio to letermovir in the range of from 0.80 to 0.90:1.00; and
- is capable of exhibiting a pH in the range of from 7 to 8, preferably from 7.4 to 7.8, when said pharmaceutical composition is dissolved in water in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In a more preferred embodiment the pharmaceutical composition according to the present invention comprises letermovir and sodium ions, wherein said pharmaceutical composition:

- comprises the sodium ions in a molar ratio to letermovir in the range of from 0.84 to 0.88:1.00; and
- is capable of exhibiting a pH in the range of from 7 to 8, preferably from 7.4 to 7.8, when said pharmaceutical composition is dissolved in water in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

- comprises the sodium ions in a molar ratio to letermovir in the range of from 0.80 to <1.00:1.00; and
- is capable of exhibiting a pH in the range of from 7 to 8, preferably from 7.4 to 7.8, when said pharmaceutical composition is dissolved in a glucose aqueous solution, preferably 5% w/v glucose solution in water, in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

- comprises the sodium ions in a molar ratio to letermovir in the range of from 0.80 to 0.90:1.00; and
- is capable of exhibiting a pH in the range of from 7 to 8, preferably from 7.4 to 7.8, when said pharmaceutical composition is dissolved in a glucose aqueous solution, preferably 5% w/v glucose solution in water, in a concentration range of from 20 to 100 mg/mL with respect to letermovir; and
- is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

- comprises the sodium ions in a molar ratio to letermovir in the range of from 0.84 to 0.88:1.00; and
- is capable of exhibiting a pH in the range of from 7 to 8, preferably from 7.4 to 7.8, when said pharmaceutical composition is dissolved in a glucose aqueous solution, preferably 5% w/v glucose solution in water, in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

comprises the sodium ions in a molar ratio to letermovir in the range of from 0.64 to <1.00:1.00; and is capable of exhibiting a pH in the range of from 7 to 8, preferably from 7.4 to 7.8, when said pharmaceutical composition is dissolved in Ringer's lactate solution in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

comprises the sodium ions in a molar ratio to letermovir in the range of from 0.72 to <1.00:1.00; and is capable of exhibiting a pH in the range of from 7 to 8, preferably from 7.4 to 7.8, when said pharmaceutical composition is dissolved in Ringer's lactate solution in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).In one embodiment the pharmaceutical composition according to the present invention comprises letermovir and sodium ions, wherein said pharmaceutical composition:

comprises the sodium ions in a molar ratio to letermovir in the range of from 0.72 to 0.90:1.00; and is capable of exhibiting a pH in the range of from 7 to 8, preferably from 7.4 to 7.8, when said pharmaceutical composition is dissolved in Ringer's lactate solution in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

comprises the sodium ions in a molar ratio to letermovir in the range of from 0.80 to 0.90:1.00; and is capable of exhibiting a pH in the range of from 7 to 8, preferably from 7.4 to 7.8, when said pharmaceutical composition is dissolved in Ringer's lactate solution in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises letermovir and sodium ions, wherein said pharmaceutical composition:

comprises the sodium ions in a molar ratio to letermovir in the range of from 0.84 to 0.88:1.00; and is capable of exhibiting a pH in the range of from 7 to 8, preferably from 7.4 to 7.8, when said pharmaceutical composition is dissolved in Ringer's lactate solution in a concentration range of from 20 to 100 mg/mL with respect to letermovir; and is essentially free from complexing solubilizing agents selected from the group consisting of PEG, lysine, arginine, and a cyclodextrin, in particular a hydroxypropyl-beta-cyclodextrin (HPBCD).

In one embodiment the pharmaceutical composition according to the present invention comprises the sodium ions in a molar ratio to letermovir in the range of from 0.50 to <1.00:1.00, preferably of from 0.55 to <1.00:1.00, more preferably of from 0.6 to <1.00:1.00, , more preferably of from 0.64 to <1.00:1.00, more preferably of from 0.65 to <1.00:1.00, more preferably of from 0.7 to <1.00:1.00, more preferably of from 0.72 to <1.00:1.00, more preferably of from 0.74 to <1.00:1.00, more preferably of from 0.76 to <1.00:1.00, more preferably of from 0.78 to <1.00:1.00, more preferably of from 0.80 to <1.00:1.00.

In one embodiment the pharmaceutical composition according to the present invention comprises the sodium ions in a molar ratio to letermovir in the range of from 0.64 to 0.90:1.00, more preferably of from 0.65 to 0.90:1.00, more preferably of from 0.72 to 0.90:1.00, more preferably of from 0.80 to 0.90:1.00, more preferably of from 0.82 to 0.90:1.00, even more preferably of from 0.84 to 0.90:1.00, even more preferably of from 0.82 to 0.88:1.00, most preferred of from 0.84 to 0.88:1.00.

In one embodiment the pharmaceutical composition according to the present invention is capable of exhibiting a pH in the range of from 7 to 8, when said pharmaceutical composition is dissolved in water in a concentration range of from 1 to 100 mg/mL with respect to letermovir. In a preferred embodiment the pharmaceutical composition according to the present invention is capable of exhibiting a pH in the range of from 7 to 8, when said pharmaceutical composition is dissolved in water in a concentration range of from 20 to 100 mg/mL with respect to letermovir.

In a preferred embodiment the pharmaceutical composition according to the present invention is capable of exhibiting a pH in the range of from 7.4 to 7.8, when said pharmaceutical composition is dissolved in water in a concentration range of from 1 to 100 mg/mL with respect to letermovir. In a more preferred embodiment the pharmaceutical composition according to the present invention is capable of exhibiting a pH in the range of from 7.4 to 7.8, when said pharmaceutical composition is dissolved in water in a concentration range of from 20 to 100 mg/mL with respect to letermovir.

In one embodiment the pharmaceutical composition according to the present invention is capable of exhibiting a pH in the range of from 7 to 8, when said pharmaceutical composition is dissolved in a glucose aqueous solution, preferably 5% w/v glucose solution in water, in a concentration range of from 20 to 100 mg/mL with respect to letermovir. In a preferred embodiment the pharmaceutical composition according to the present invention is capable of exhibiting a pH in the range of from 7.4 to 7.8, when said pharmaceutical composition is dissolved in a glucose aqueous solution, preferably 5% w/v glucose solution in water, in a concentration range of from 20 to 100 mg/mL with respect to letermovir.

In one embodiment the pharmaceutical composition according to the present invention is capable of exhibiting a pH in the range of from 7 to 8, when said pharmaceutical composition is dissolved in Ringer's lactate solution in a concentration range of from 20 to 100 mg/mL with respect to letermovir. In a preferred embodiment the pharmaceutical composition according to the present invention is capable of exhibiting a pH in the range of from 7.4 to 7.8, when said pharmaceutical composition is dissolved in Ringer's lactate solution in a concentration range of from 20 to 100 mg/mL with respect to letermovir.

In one embodiment a pharmaceutical composition comprising letermovir of formula (I), and sodium ions (I)

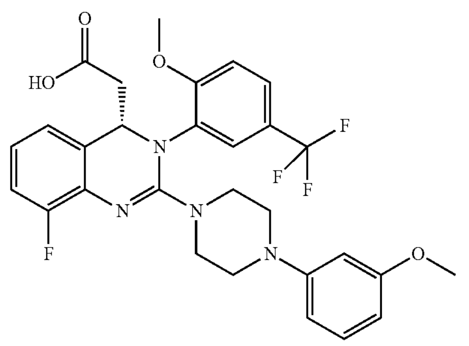

wherein the pharmaceutical composition comprises the sodium ions in a molar ratio to letermovir in the range of from 0.50 to <1.00:1.00, preferably of from 0.80 to 0.90:1.00; and is capable of exhibiting a pH in the range of from 7 to 8, preferably 7.4 to 7.8, when said pharmaceutical composition is dissolved in water in a concentration range of from 1 to 100 mg/mL with respect to letermovir; and is essentially free from complexing solubilizing agents selected from the group consisting of PEG, lysine, arginine, a cyclodextrin, in particular a hydroxypropyl-beta-cyclodextrin (HPBCD), further comprises at least one pharmaceutical carrier or excipient.

In one embodiment a pharmaceutical composition comprising letermovir of formula (I), and sodium ions (I)

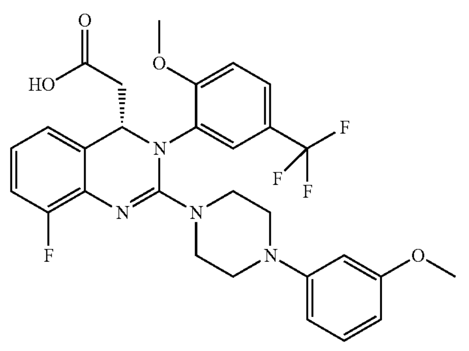

wherein the pharmaceutical composition comprises the sodium ions in a molar ratio to letermovir in the range of from 0.80 to <1.00:1.00, more preferably of from 0.80 to 0.90:1.00; and is capable of exhibiting a pH in the range of from 7 to 8, preferably from 7.4 to 7.8, when said pharmaceutical composition is dissolved in a glucose aqueous solution, preferably 5% w/v glucose solution in water, in a concentration range of from 1 to 100 mg/mL, preferably 20 to 100 mg/mL, with respect to letermovir; and is essentially free from complexing solubilizing agents selected from the group consisting of PEG, lysine, arginine, a cyclodextrin, in particular a hydroxypropyl-beta-cyclodextrin (HPBCD), further comprises at least one pharmaceutical carrier or excipient.

In one embodiment a pharmaceutical composition comprising letermovir of formula (I), and sodium ions (I)

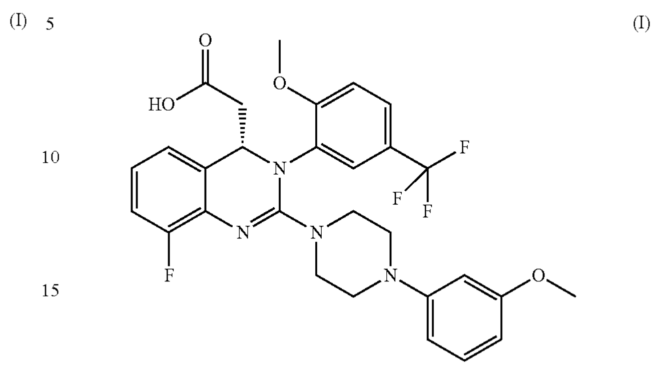

wherein the pharmaceutical composition comprises the sodium ions in a molar ratio to letermovir in the range of from 0.64 to <1.00:1.00, more preferably of from 0.72 to <1.00:1.00, more preferably of from 0.80 to <1.00:1.00, more preferably of from 0.80 to 0.90:1.00; and is capable of exhibiting a pH in the range of from 7 to 8, preferably from 7.4 to 7.8, when said pharmaceutical composition is dissolved in Ringer's lactate solution in a concentration range of from 1 to 100 mg/mL, preferably 20 to 100 mg/mL, with respect to letermovir; and is essentially free from complexing solubilizing agents selected from the group consisting of PEG, lysine, arginine, a cyclodextrin, in particular a hydroxypropyl-beta-cyclodextrin (HPBCD), further comprises at least one pharmaceutical carrier or excipient.

In one embodiment a pharmaceutical composition according to the invention comprises at least one excipient selected from the group consisting of a carbohydrate, such as sucrose or mannitol; an amino acid, such as phenylalanine; a polyalkoxy compound, such as a poloxamer, more particular poloxamer 188; and a polyvinylpyrrolidone (PVP), such as PVP PF12. In a preferred embodiment said excipient is mannitol or sucrose or a combination thereof.

In one embodiment a pharmaceutical composition according to the invention is essentially free from complexing solubilizing agents.

In one embodiment a pharmaceutical composition according to the invention may contain an excipient which exhibits complexing solubilizing properties. In one embodiment such an excipient is a polyalkoxy compound, such as a poloxamer. In one embodiment, the poloxamer is poloxamer 188.

In one embodiment, the pharmaceutical composition according to the invention comprises a polyalkoxy compound, such as a poloxamer, such as poloxamer 188, and is essentially free from other complexing solubilizing agents.

In one embodiment the used excipients are suitable for administration to subjects in the need of particular solid-organ transplantation, e.g. subjects with kidney damages and subjects in need of allogenic hematopoietic stem cell transplantation. Non-limiting examples of such excipients include sucrose, mannitol, phenylalanine, and a poloxamer, such as poloxamer 188, and a polyvinylpyrrolidone (PVP), such as PVP PF12.

In one embodiment a pharmaceutical composition according to the invention further comprises a buffer, preferably Tris hydroxy aminomethane (Tris).

In one embodiment a pharmaceutical composition according to the invention further comprises HCl.

In one embodiment a pharmaceutical composition according to the invention represents a stability in accordance with ICH QIA (R2) (Stability testing of new drug substances and drug products) covering the climate zones I to IV. In a preferred embodiment a pharmaceutical composition according to the invention is stable for at least one month. In a more preferred embodiment a pharmaceutical composition according to the invention is stable for at least three months. In a more preferred embodiment a pharmaceutical composition according to the invention is stable for at least 6 months. In a more preferred embodiment a pharmaceutical composition according to the invention is stable for at least 12 months. In a more preferred embodiment a pharmaceutical composition according to the invention is stable for at least 18 months. In a more preferred embodiment a pharmaceutical composition according to the invention is stable for at least 36 months.

In one embodiment a pharmaceutical composition according to the invention is in a solid form. In a preferred embodiment said solid form of said pharmaceutical composition is a lyophilizate.

In one embodiment a pharmaceutical composition according to the invention is in a liquid form. In a preferred embodiment said liquid form of a pharmaceutical composition according to the invention is an aqueous solution. In another preferred embodiment said liquid form of a pharmaceutical composition according to the invention is a solution in at least one parenterally acceptable diluent. Non-limiting examples of parenterally acceptable diluents include water, glucose aqueous solution and Ringer's lactate solution.

In one embodiment a pharmaceutical composition according to the invention is suitable for intravenous (IV) application or for injection.

The subject-matter of the present invention further relates to a method of producing the pharmaceutical composition according to the invention, comprising the following step:

i) providing a solution of letermovir and sodium ions, wherein the molar ratio of sodium ions to letermovir is in the range of from 0.50 to <1.00:1.00, preferably 0.64 to <1.00:1.00, more preferably of from 0.65 to <1.00:1.00, more preferably of from 0.72 to <1.00:1.00, more preferably of from 0.80 to <1.00:1.00, more preferably of from 0.80 to 0.90:1.00, in particular in the range of from 0.84 to 0.88:1.00; and optionally at least one excipient selected from the group consisting of a carbohydrate, in particular sucrose or mannitol, an amino acid, in particular phenylalanine, a polyalkoxy compound, in particular a poloxamer, more particular poloxamer 188, and a polyvinylpyrrolidone (PVP), in particular PVP PF12.

In one embodiment the solution provided in step i above is a solution in a parenterally acceptable diluent, such as water.

In one embodiment providing the solution according to step i above comprises the following steps:

a-1) providing a suspension of letermovir in a parenterally acceptable diluent, in particular water;

b-1) adding NaOH to the suspension obtained in step a-1 to provide a mixture;

c-1) optionally stirring the mixture obtained in step b-1 for at least 30 min.

d-1) optionally adding at least one excipient selected from the group consisting of a carbohydrate, in particular sucrose and mannitol, an amino acid, in particular phenylalanine, a polyalkoxy compound, in particular a poloxamer, more particular poloxamer 188, and a polyvinylpyrrolidone (PVP), in particular PVP PF12 to said mixture;

e-1) optionally stirring said mixture for at least 30 min.

In a preferred embodiment, an aqueous solution of NaOH is added in step b-1.

In a preferred embodiment, the solution in step c-1 is stirred for at least 2 hours.

In a preferred embodiment, the solution in step e-1 is stirred for at least 2 hours.

In a preferred embodiment 0.64 to <1.00 equivalents of NaOH with respect to letermovir are added in step b-1. In a more preferred embodiment 0.65 to <1.00 equivalents of NaOH with respect to letermovir are added in step b-1. In a more preferred embodiment 0.72 to <1.00 equivalents of NaOH with respect to letermovir are added in step b-1. In a more preferred embodiment 0.80 to <1.00 equivalents of NaOH with respect to letermovir are added in step b-1.

In a preferred embodiment 0.64 to 0.90 equivalents of NaOH with respect to letermovir are added in step b-1. In a more preferred embodiment 0.65 to 0.90 equivalents of NaOH with respect to letermovir are added in step b-1. In a more preferred embodiment 0.72 to 0.90 equivalents of NaOH with respect to letermovir are added in step b-1. In a more preferred embodiment 0.80 to 0.90 equivalents of NaOH with respect to letermovir are added in step b-1. In a more preferred embodiment 0.84 to 0.88 equivalents of NaOH with respect to letermovir are added in step b-1.

In one embodiment 0.64 equivalents of NaOH with respect to letermovir are added in step b-1. In one embodiment 0.65 equivalents of NaOH with respect to letermovir are added in step b-1. In one embodiment 0.72 equivalents of NaOH with respect to letermovir are added in step b-1. In one embodiment 0.80 equivalents of NaOH with respect to letermovir are added in step b-1. In one embodiment 0.82 equivalents of NaOH with respect to letermovir are added in step b-1. In one embodiment 0.84 equivalents of NaOH with respect to letermovir are added in step b-1. In one embodiment 0.86 equivalents of NaOH with respect to letermovir are added in step b-1. In one embodiment 0.88 equivalents of NaOH with respect to letermovir are added in step b-1. In one embodiment 0.90 equivalents of NaOH with respect to letermovir are added in step b-1.

In another embodiment the method for providing a solution according to step i comprises utilizing the following steps a-2 to e-2 in place of steps a-1 to e-1:

a-2) providing a solution of NaOH in a parenterally acceptable diluent, in particular water;

b-2) adding letermovir to the solution obtained in step a-2 to provide a mixture;

c-2) optionally stirring the mixture obtained in step b-2 for at least 30 minl;

d-2) optionally adding at least one excipient selected from the group consisting of a carbohydrate, in particular sucrose and mannitol, an amino acid, in particular phenylalanine, a polyalkoxy compound, in particular a poloxamer, more particular poloxamer 188, and a polyvinylpyrrolidone (PVP), in particular PVP PF12 to said mixture;

e-2) optionally stirring said mixture for at least 30 minl.

In a preferred embodiment, the solution in step c-2 is stirred for at least 2 hours.

In a preferred embodiment, the solution in step e-2 is stirred for at least 2 hours.

In a preferred embodiment 1.56 to >1.00 equivalents of letermovir with respect to NaOH are added in step b-2. In a more preferred embodiment 1.54 to >1.00 equivalents of letermovir with respect to NaOH are added in step b-2. In a more preferred embodiment 1.39 to >1.00 equivalents of letermovir with respect to NaOH are added in step b-2. In a more preferred embodiment 1.25 to >1.00 equivalents of letermovir with respect to NaOH are added in step b-2.

In a preferred embodiment 1.56 to 1.11 equivalents of letermovir with respect to NaOH are added in step b-2. In a more preferred embodiment 1.54 to 1.11 equivalents of letermovir with respect to NaOH are added in step b-2. In a more preferred embodiment 1.39 to 1.11 equivalents of letermovir with respect to NaOH are added in step b-2. In a more preferred embodiment 1.25 to 1.11 equivalents of letermovir with respect to NaOH are added in step b-2. In a more preferred embodiment 1.19 to 1.14 equivalents of letermovir with respect to NaOH are added in step b-2.

In one embodiment 1.56 equivalents of letermovir with respect to NaOH are added in step b-2. In one embodiment 1.54 equivalents of letermovir with respect to NaOH are added in step b-2. In one embodiment 1.39 equivalents of letermovir with respect to NaOH are added in step b-2. In one embodiment 1.25 equivalents of letermovir with respect to NaOH are added in step b-2. In one embodiment 1.22 equivalents of letermovir with respect to NaOH are added in step b-2. In one embodiment 1.19 equivalents of letermovir with respect to NaOH are added in step b-2. In one embodiment 1.16 equivalents of letermovir with respect to NaOH are added in step b-2. In one embodiment 1.14 equivalents of letermovir with respect to NaOH are added in step b-2. In one embodiment 1.11 equivalents of letermovir with respect to NaOH are added in step b-2.

In one embodiment the method of producing the pharmaceutical composition according to the present invention further comprises adjusting the pH of the solution obtained in step i to a range of from 7 to 8, preferably from 7.4 to 7.8. In one preferred embodiment said adjustment is performed by adding HCl. In a more preferred embodiment the pH of the solution obtained in step i is in the range of from 7 to 8, preferably from 7.4 to 7.8 and the pH adjustment is not necessary.

In one embodiment the solution obtained after the pH adjustment is optionally stirred for at least 10 min, preferably at least 30 min.

In one embodiment the method of producing the pharmaceutical composition according to the present invention optionally comprises filtering the solution obtained in step i. In one embodiment the method of producing the pharmaceutical composition according to the present invention optionally comprises filtering the solution obtained after adjustment of the pH of the solution obtained in step i above.

In one embodiment the method of producing the pharmaceutical composition according to the present invention further comprises freeze-drying the obtained solution to provide a lyophilizate.

In one embodiment the method of producing the pharmaceutical composition according to the present invention further comprises reconstituting the lyophilizate in a first parenterally acceptable diluent to provide a reconstituted solution in a concentration range of from 0.1 to 100 mg/mL with respect to letermovir and optionally further diluting said reconstituted solution with a second parenterally acceptable diluent to a final concentration which is acceptable for injection or infusion. Said first and said second parenterally acceptable diluents can be the same or different. In one embodiment said reconstituted solution exhibits a pH a range of from 7 to 8, preferably from 7.4 to 7.8, when letermovir is present in a concentration range of from 0.1 to 100 mg/mL in said reconstituted solution. In a preferred embodiment said reconstituted solution exhibits a pH in a range of from 7 to 8, preferably from 7.4 to 7.8, when letermovir is present in a concentration range of from 20 to 100 mg/mL in said reconstituted solution.

In one embodiment the final concentration which is acceptable for injection or infusion is in a range from 0.1 to 100 mg/mL. In another embodiment the final concentration which is acceptable for injection or infusion is in a range from 0.8 to 100 mg/mL. In another embodiment the final concentration which is acceptable for injection or infusion is in a range from 20 to 100 mg/mL. In another embodiment the final concentration which is acceptable for injection or infusion is in a range from 50 to 100 mg/mL. In another embodiment the final concentration which is acceptable for injection or infusion is in a range from 20 to 50 mg/mL. In a preferred embodiment the final concentration which is acceptable for injection or infusion is 0.8 mg/mL.

In a preferred embodiment the method of producing the pharmaceutical composition according to the present invention comprises the following steps:

i) providing a solution of letermovir and sodium ions, wherein the molar ratio of sodium ions to letermovir is in the range of from 0.50 to <1.00:1.00, preferably 0.64 to <1.00:1.00, more preferably of from 0.65 to <1.00:1.00, more preferably of from 0.72 to <1.00:1.00, more preferably of from 0.80 to <1.00:1.00, more preferably of from 0.80 to 0.90:1.00, in particular in the range of from 0.84 to 0.88:1.00; and optionally at least one excipient selected from the group consisting of a carbohydratesuch as sucrose or mannitol; an amino acidsuch as phenylalanine; a polyalkoxy compound such as a poloxamer, particularly poloxamer 188; and a polyvinylpyrrolidone (PVPsuch as PVP PF12;
ii) if needed adjusting the pH of the solution obtained in step i to a range of from 7 to 8, preferably from 7.4 to 7.8, with a suitable organic and inorganic acid;
iii) optionally filtering the obtained solution.

In one embodiment of step ii the organic or inorganic acid is HCl.

In another preferred embodiment the method of producing the pharmaceutical composition according to the present invention comprises the following steps:

i) providing a solution of letermovir and sodium ions, wherein the molar ratio of sodium ions to letermovir is in the range of from 0.50 to <1.00:1.00, preferably 0.64 to <1.00:1.00, more preferably of from 0.65 to <1.00:1.00, more preferably of from 0.72 to <1.00:1.00, more preferably of from 0.80 to <1.00:1.00, more preferably of from 0.80 to 0.90:1.00, in particular in the range of from 0.84 to 0.88:1.00; and optionally at least one excipient selected from the group consisting of a carbohydratesuch as sucrose or mannitol; an amino acidsuch as phenylalanine; a polyalkoxy compound such as a poloxamer, particularly poloxamer 188; and a polyvinylpyrrolidone (PVPsuch as PVP PF12;
ii) if needed adjusting the pH of the solution obtained in step i to a range of from 7 to 8, preferably from 7.4 to 7.8, with a suitable organic and inorganic acid;
iii) optionally filtering the obtained solution;
iv) freeze-drying the obtained solution to provide a lyophilizate.

In one embodiment of step ii the organic or inorganic acid is HCl.

In another preferred embodiment the method of producing the pharmaceutical composition according to the present invention comprises the following steps:

i) providing a solution of letermovir and sodium ions, wherein the molar ratio of sodium ions to letermovir is in the range of from 0.50 to <1.00:1.00, preferably 0.64 to <1.00:1.00, more preferably of from 0.65 to <1.00:1.00, more preferably of from 0.72 to <1.00:1.00, more preferably of from 0.80 to <1.00:1.00, more preferably of from 0.80 to 0.90:1.00, in particular in the range of from 0.84 to 0.88:1.00; and optionally at least one excipient selected from the group consisting of a carbohydratesuch as sucrose or mannitol; an amino acidsuch as phenylalanine; a polyalkoxy compound such as a poloxamer, particularly poloxamer 188; and a polyvinylpyrrolidone (PVP), such as PVP PF12.
ii) if needed adjusting the pH of the solution obtained in step i to a range of from 7 to 8, preferably from 7.4 to 7.8, with a suitable organic and inorganic acid;
iii) optionally filtering the obtained solution;
iv) freeze-drying the obtained solution to provide a lyophilizate;
v) reconstituting the lyophilizate in a first parenterally acceptable diluent to provide a reconstituted solution in a concentration range of from 1 to 100 mg/mL, preferably of from 20 to 100 mg/mL with respect to letermovir and optionally further diluting said reconstituted solution with a second parenterally acceptable diluent to a final concentration which is acceptable for injection or infusion, wherein said first and said second parenterally acceptable diluents can be identical or different from each other.

In one embodiment of step ii the organic or inorganic acid is HCl.

The above steps i to v do not necessarily signify a specific sequence or number of steps. However, preferably the steps of the method are implemented in the order as shown above. Some of said steps may be optional and in some embodiments optional steps are not implemented. For example in one embodiment step ii may directly be followed by step iv without implementation of step iii. Also the above shown steps do not exclude additional steps that are not explicitly mentioned. For example, the solution obtained in step i and/or ii may be optionally stirred.

The subject-matter of the present invention further relates to a pharmaceutical composition, which is obtainable by any method disclosed herein.

The pharmaceutical compositions according to the invention may be used to produce drugs which are suitable for use in methods of preventing and/or treating infections with a representative of the Herpes viridae group, in particular a cytomegalovirus, in particular the human cytomegalovirus.

Further subject matter of the present invention the pharmaceutical compositions according to the invention for use in the method of treating and/or preventing diseases, preferably viral infections, in particular infections with the human cytomegalovirus (HCMV) or another representative of the Herpes viridae group.

An additional aspect of the present invention relates to the use of the pharmaceutical compositions according to the invention in the method of treating and/or preventing diseases, preferably viral infections, in particular infections with the human cytomegalovirus (HCMV) or another representative of the Herpes viridae group.

Another aspect of the present invention relates to the use of the pharmaceutical composition according to the invention for the preparation of a medicament for the treatment and/or preventing of diseases, in particular of viral infections, preferably human cytomegalovirus (HCMV) infections or infections with another member of the herpes viridae group.

Still another aspect of the present invention relates to the method of the treatment and/or preventing virus infections, preferably human cytomegalovirus (HCMV) infections or infections with another member of the herpes viridae group, in a subject in need thereof by administering a pharmaceutical composition according to the invention. In one embodiment said subject is selected from the group consisting of neonates, subjects in the need of particular solid-organ transplantation, e.g. subjects with kidney damages and subjects in need of allogenic hematopoietic stem cell transplantation.

In general, it has proven to be advantageous to administer the pharmaceutical compositions in such a way that about 0.001 to 10 mg per kg, preferably 0.01 to 5 mg per kg body weight of 2-[(4S)-8-fluoro-2-[4-(3-methoxyphenyl)piperazin-1-yl]-3-[2-methoxy-5-(trifluoromethyl)phenyl]-4H-quinazolin-4-yl]acetatic acid (letermovir) is administered.

Nevertheless, it may be necessary to deviate from the stated amounts of letermovir, namely depending on body weight, individual response to the active substance and the time and interval at which it is administered. For example, in certain cases it may be sufficient to administer less than the aforementioned minimum amount of letermovir, while in other cases the stated upper limit may be exceeded. When administering large amounts it may be recommendable to distribute these in several individual doses over the course of a day.

The invention will now be described in detail on the basis of non-restrictive examples.

Unless otherwise stated, the percentages given in the following tests and examples are weight percentages, parts are weight proportions, solvent ratios, dilution ratios and concentrations of liquid solutions relate, in each case, to the volume.

Abbreviations

API active pharmaceutical ingredient
h hour(s)
HCl hydrochloric acid
HEPES (4-(2-hydroxyethyl)-1-piperazineethanesulfonic acid)
HPBCD hydroxypropyl-beta-cyclodextrin
HPLC high pressure liquid chromatography
conc. concentrated
min. minutes
LAF laminar air flow
PEG polyethylene glycol
PDE permissible daily exposures
$R_T$ retention time (in HPLC)
RP-HPLC reversed phase high pressure liquid chromatography
rpm revolutions per minute
rt room temperature Analytical Methods Visual Inspection The samples were inspected for the presence or absence of visible particles under gentle, manual, radial agitation for 5 seconds in front of a white background.

pH

The pH value of the samples was measured with a calibrated pH meter EUTEGH CAKTON PH/Ion 510 Serial n° 172361 with a Polilyte lab electrode. The sample is stirred and the electrode is introduced. A measurement is performed until the pH value is stable. Between measurements the electrode is thoroughly rinsed with water. The pH measurements were performed with an analysis volume of ~1-2 mL and a defined temperature of 22° C.±3° C. A 3-point calibration of the pH meter was performed on a daily basis, by using buffers with pH 7.00, pH 4.01 and pH 10.01 (Hamilton Duracal buffer).

Reversed-Phase High Performance Liquid Chromatography (RP-HPLC)

RP-HPLC was used to determine the concentration of letermovir free base and potential degradation products.

Table 1 gives an overview of the eluents that were used for RP-HPLC analysis.

TABLE 1

Eluents to be used for RP-HPLC analysis.

| Eluents | Preparation |
|---|---|
| Eluent A: (0.1% formic acid in water) | Add 500 μl formic acid to a volumetric flask and fill up to 500 ml with highly purified water |
| Eluent B: (0.1% formic acid in methanol) | Add 500 μl formic acid to a volumetric flask and fill up to 500 ml with methanol |

The following parameters were used for the RP-HPLC method:

Instrument: Agilent Technologies 1200 series with a VWD G131413 detector

Column: Agilent Zorbax Eclipse XDB C-18, 150×4.6 mm, 5 μm

Flow rate: 1.0 m/min

Solvent A: 0.1% formic acid in water

Solvent B: 0.1% formic acid in 100% methanol

Stop time: 26 minutes

Injection volume: 10 μl

Column temperature: 35° C.

Wavelength: 260 nm

Table 2 shows the gradient that was used for the RP-HPLC method.

TABLE 2

Gradient applied during RP-HPLC analysis.

| Time [min] | Eluent B [%] |
|---|---|
| 0.00 | 5.0 |
| 1.00 | 5.0 |
| 20.00 | 95.0 |
| 23.00 | 95.0 |
| 23.10 | 5.0 |
| 26.00 | 5.0 |

A calibration curve of the reference standard was used for the quantification of letermovir free base in solution.

The samples were diluted to approximately 2 mg/mL in water (corrected for letermovir free base in solution) and analyzed with an injection volume of 10 μl. Prior to injection, the diluted samples were filtered through a syringe filter (nylon, 0.45 μm).

Peak integration was performed manually for all API-related peaks. Peaks that were also present in blank or formulation buffer injections were neglected.

Powder X-Ray Diffraction (PXRD)

Equipment: Powder diffraction patterns were acquired on a Bruker D8 Advance Series 2Theta/theta powder diffraction system using CuKα1-radiation in transmission geometry. The system is equipped with a VANTEC-1 single photon counting PSD, a Germanium monochromator, fixed divergence slits and a radial soller. Software used: Data collection with DIFFRAC plus XRD Commander V. 2.5.1, and evaluation with EVA V. 5.0.0.22 (Bruker-AXS 2010-2018).

Sample preparation: Approximately 15 mg of non-manipulated sample were prepared in standard sample holders using two foils of polyacetate.

Measurement conditions: The samples were measured at room temperature in a range from 4° to 40° in 2θ in a 0.1 hours measurement using an angular step of 0.049° and a time per step of 2787 s.

Examples

Example 1. Study of the Solubility and pH of Solutions of Different Letermovir Forms and Solutions of Letermovir Free Base with Different Equivalents of NaOH A first set of letermovir samples was prepared by dissolving letermovir free base, letermovir sodium salt amorphous, letermovir sodium salt trihydrate or letermovir sodium salt monohydrate in water to prepare the solutions with the concentration of 20 mg/mL and 100 mg/mL with respect to letermovir free base in order to determine the differences in the pH immediately after dissolution and after 1 week and to check precipitation effects and solubility.

A second set of samples was prepared by adding different equivalents of sodium hydroxide (0.84, 0.86, 0.88 and 0.9 eq.) to letermovir free base solutions. Blank solutions with the same amounts of water and sodium hydroxide equivalents and without letermovir were also prepared for comparative reasons.

Letermovir free base and the letermovir sodium salt amorphous were dried in a vacuum oven at 90° C. (ca. 5 mbar) overnight in order to remove residual water.

a) Initial Drying

Procedure: 2 samples of letermovir sodium amorphous and 10 samples of letermovir free base were prepared by weighing the corresponding substance and drying in a vacuum oven at 90° C. (ca. 5 mbar) overnight in order to remove residual water and to avoid weighing errors to calculate the equivalents of NaOH (Table 3).

Samples of ca. 80 mg and 300 mg were weighed to be dissolved in 4 mL and 3 mL, respectively, to prepare the solutions with the concentration of 20 mg/mL and 100 mg/mL with respect to letermovir free base.

TABLE 3

Initial drying process of twelve samples of letermovir sodium amorphous and letermovir free base.

| Letermovir form | Starting material, g | Sample lost, g | Final weight, g | Real free base, g |
|---|---|---|---|---|
| Sodium Salt Amorphous | 0.0838 | 0.0136 | 0.0702 | 0.0675 |
| Sodium Salt Amorphous | 0.3126 | 0.0418 | 0.2708 | 0.2603 |
| Free Base | 0.0811 | 0.0041 | 0.0770 | 0.0770 |
| Free Base | 0.3014 | 0.0083 | 0.2931 | 0.2931 |
| Free Base | 0.0802 | 0.0041 | 0.0761 | 0.0761 |

TABLE 3-continued

Initial drying process of twelve samples of letermovir sodium amorphous and letermovir free base.

| Letermovir form | Starting material, g | Sample lost, g | Final weight, g | Real free base, g |
|---|---|---|---|---|
| Free Base | 0.0812 | 0.0041 | 0.0771 | 0.0771 |
| Free Base | 0.0812 | 0.0041 | 0.0771 | 0.0771 |
| Free Base | 0.0811 | 0.0036 | 0.0775 | 0.0775 |
| Free Base | 0.3003 | 0.0078 | 0.2925 | 0.2925 |
| Free Base | 0.3004 | 0.0080 | 0.2924 | 0.2924 |
| Free Base | 0.3008 | 0.0075 | 0.2933 | 0.2933 |
| Free Base | 0.3014 | 0.0077 | 0.2937 | 0.2937 |

b) Preparation of Suspensions/Solutions and Analysis of DpH and Solubility

Procedure: The corresponding amount of water was added to each sample with further addition of the respective equivalents of 1 M aqueous NaOH to the samples of second set (Table 4, Table 5 and Table 6). No addition of NaOH was applied to the first set of samples.

The suspensions were stirred at room temperature and the pH was determined immediately after the preparation and after 1 week. The solubility and precipitation effects were also checked (Table 7, Table 8 and Table 9).

TABLE 4

Preparation of samples of different letermovir forms in water.

| Letermovir form | Equivalents of NaOH | Real free base, g | Concentration with respect to free base | mL of $H_2O$ |
|---|---|---|---|---|
| Sodium Salt Trihydrate | — | 0.0802 | 20 mg/mL | 4.01 |
| Sodium Salt Trihydrate | — | 0.3003 | 100 mg/mL | 3.00 |
| Sodium Salt Monohydrate | — | 0.0405 | 20 mg/mL | 2.02 |
| Sodium Salt Monohydrate | — | 0.2003 | 100 mg/mL | 2.00 |
| Sodium Salt Amorphous | — | 0.0675 | 20 mg/mL | 3.37 |
| Sodium Salt Amorphous | — | 0.2603 | 100 mg/mL | 2.60 |
| Free Base | — | 0.0770 | 20 mg/mL | 3.85 |
| Free Base | — | 0.2931 | 100 mg/mL | 2.93 |

TABLE 5

Preparation of samples of letermovir free base in water and with different equivalents of NaOH.

| Letermovir Free Base Concentration [mg/ml] | NaOH/Letermovir Molar Ratio | Real free base, g | μL of 1M $NaOH_{aq}$ 1M | mL of $H_2O$ |
|---|---|---|---|---|
| 20 | 0.84/1 | 0.0761 | 111.65 | 3.69 |
| 100 | 0.84/1 | 0.2925 | 429.13 | 2.50 |
| 20 | 0.86/1 | 0.0771 | 115.81 | 3.74 |
| 100 | 0.86/1 | 0.2924 | 439.19 | 2.48 |
| 20 | 0.88/1 | 0.0771 | 118.50 | 3.74 |
| 100 | 0.88/1 | 0.2933 | 450.79 | 2.48 |
| 20 | 0.90/1 | 0.0775 | 121.82 | 3.75 |
| 100 | 0.90/1 | 0.2937 | 461.66 | 2.48 |

TABLE 6

Preparation of the samples without letermovir free base (Blanks).

| Letermovir form | Equivalents of NaOH | μL of $NaOH_{aq}$ 1M | mL of $H_2O$ |
|---|---|---|---|
| — | 0.84 | 112 | 3.69 |
| — | 0.84 | 429 | 2.50 |
| — | 0.86 | 116 | 3.74 |
| — | 0.86 | 439 | 2.48 |
| — | 0.88 | 119 | 3.74 |
| — | 0.88 | 451 | 2.48 |
| — | 0.90 | 122 | 3.75 |
| — | 0.90 | 462 | 2.48 |

TABLE 7

Analysis of pH and solubility of samples of different letermovir forms in water.

| Letermovir form [mg/ml] | Initial pH | pH after 1 week | Solubility/ Precipitation |
|---|---|---|---|
| Sodium Salt Trihydrate 20 mg/ml | 9.5 | 9.2 | Clear solution |
| Sodium Salt Trihydrate 100 mg/ml | 9.5 | 9.2 | Clear solution |
| Sodium Salt Monohydrate 20 mg/ml | 9.2 | 8.9 | Clear solution |
| Sodium Salt Monohydrate 100 mg/ml | 9.2 | 9.0 | Clear solution |
| Sodium Salt Amorphous 20 mg/ml | 9.2 | 9.0 | Clear solution |
| Sodium Salt Amorphous 100 mg/ml | 9.3 | 9.1 | Clear solution |
| Free Base 20 mg/ml | 6.1 | 6.1 | Insoluble |
| Free Base 100 mg/ml | 6.3 | 6.2 | Insoluble |

TABLE 8

Analysis of pH and solubility of samples of letermovir Free Base in water and with different equivalents of NaOH.

| Letermovir Free Base Concentration [mg/ml] | NaOH/Letermovir Molar Ratio | Initial pH | pH after 1 week | Solubility/ Precipitation |
|---|---|---|---|---|
| 20 | 0.84/1 | 7.7 | 7.7 | * |
| 100 | 0.84/1 | 7.6 | 7.6 | * |
| 20 | 0.86/1 | 7.7 | 7.7 | * |
| 100 | 0.86/1 | 7.6 | 7.6 | * |
| 20 | 0.88/1 | 7.9 | 7.8 | * |
| 100 | 0.88/1 | 7.7 | 7.7 | * |
| 20 | 0.90/1 | 8.2 | 7.9 | * |
| 100 | 0.90/1 | 7.8 | 7.7 | * |

*Some particles were in suspension, but after 24 h, there were observed only few particles above the solution (interphase air-water).

TABLE 9

Analysis of pH and solubility of solutions without letermovir free base (Blanks).

| Letermovir form | Equivalents of NaOH | Initial pH | pH after 1 week | Solubility/ Precipitation |
|---|---|---|---|---|
| — | 0.84 for 20 mg letermovir | 12.3 | 12.3 | Clear solution |
| — | 0.84 for 100 mg letermovir | 12.7 | 12.7 | Clear solution |

TABLE 9-continued

| Analysis of pH and solubility of solutions without letermovir free base (Blanks). | | | | |
|---|---|---|---|---|
| Letermovir form | Equivalents of NaOH | Initial pH | pH after 1 week | Solubility/ Precipitation |
| — | 0.86 for 20 mg letermovir | 12.3 | 12.3 | Clear solution |
| — | 0.86 for 100 mg letermovir | 12.7 | 12.7 | Clear solution |
| — | 0.88 for 20 mg letermovir | 12.3 | 12.3 | Clear solution |
| — | 0.88 for 100 mg letermovir | 12.7 | 12.7 | Clear solution |
| — | 0.90 for 20 mg letermovir | 12.3 | 12.3 | Clear solution |
| — | 0.90 for 100 mg letermovir | 12.7 | 12.7 | Clear solution |

Results

The pH values of the solutions of letermovir sodium dalt trihydrate, letermovir sodium salt monohydrate and letermovir sodium salt amorphous in water were always between 9 and 9.5. No significant differences were observed after 1 week. The solutions were completely clear without precipitation effects over time as determined by visual inspection. The pH of the suspension of letermovir free base in water without sodium hydroxide was around 6. The suspension did not dissolve over 1 week.

The pH of the solutions of letermovir free base in water with different equivalents of sodium hydroxide (0.84-0.9 eq.) was around 7.8. A small amount of particles was only observed on the interphase air-water interphase after 24 h.

The blank solutions prepared without letermovir free base and with only sodium hydroxide, were clear and pH was around 12.5.

Example 2. Monitoring of Solutions of Letermovir Free Base with Different Equivalents of Sodium Hydroxide at Different Temperatures a) Initial Drying 26 samples of letermovir free base were prepared by weighing the substance and drying in a vacuum oven at 90° C. (ca. 5 mbar) overnight in order to remove residual water and to avoid weighing errors to calculate the equivalents of NaOH (Table 10).

Samples of ca. 80 mg and 300 mg were weighed to be dissolved in 4 mL and 3 mL, respectively, to prepare 20 mg/mL and 100 mg/mL solutions.

TABLE 10

| Initial drying process of 26 samples of letermovir free base | | | | | |
|---|---|---|---|---|---|
| Planned Letermovir Free Base concentration [mg/ml] | Temperature During Dissolution | Planned NaOH/Letermovir Molar Ratio | Starting material, g | Sample lost, g | Final weight, g |
| 20 | rt | 0.80/1 | 0.0806 | 0.0041 | 0.0765 |
| 20 | rt | 0.82/1 | 0.0802 | 0.0045 | 0.0757 |
| 20 | rt | 0.84/1 | 0.0802 | 0.0041 | 0.0761 |
| 20 | rt | 0.86/1 | 0.0812 | 0.0041 | 0.0771 |
| 20 | rt | 0.88/1 | 0.0812 | 0.0041 | 0.0771 |
| 20 | rt | 0.90/1 | 0.0811 | 0.0036 | 0.0775 |
| 20 | rt | 1/1 | 0.0801 | 0.0036 | 0.0765 |
| 100 | rt | 0.80/1 | 0.3009 | 0.0079 | 0.2930 |
| 100 | rt | 0.82/1 | 0.3009 | 0.0077 | 0.2932 |
| 100 | rt | 0.84/1 | 0.3003 | 0.0078 | 0.2925 |
| 100 | rt | 0.86/1 | 0.3004 | 0.0080 | 0.2924 |
| 100 | rt | 0.88/1 | 0.3008 | 0.0075 | 0.2933 |
| 100 | rt | 0.90/1 | 0.3014 | 0.0077 | 0.2937 |
| 100 | rt | 1/1 | 0.3018 | 0.0075 | 0.2943 |
| 20 | 40° C. | 0.84/1 | 0.0805 | 0.0038 | 0.0767 |
| 20 | 40° C. | 0.86/1 | 0.0808 | 0.0027 | 0.0781 |
| 20 | 40° C. | 0.88/1 | 0.0814 | 0.0038 | 0.0776 |
| 20 | 60° C. | 0.84/1 | 0.0811 | 0.0034 | 0.0777 |
| 20 | 60° C. | 0.86/1 | 0.0804 | 0.0037 | 0.0767 |
| 20 | 60° C. | 0.88/1 | 0.0810 | 0.0031 | 0.0779 |
| 100 | 40° C. | 0.84/1 | 0.3014 | 0.0075 | 0.2939 |
| 100 | 40° C. | 0.86/1 | 0.3004 | 0.0075 | 0.2929 |
| 100 | 40° C. | 0.88/1 | 0.3010 | 0.0070 | 0.2940 |
| 100 | 60° C. | 0.84/1 | 0.3011 | 0.0077 | 0.2934 |
| 100 | 60° C. | 0.86/1 | 0.3018 | 0.0075 | 0.2943 |
| 100 | 60° C. | 0.88/1 | 0.0805 | 0.0038 | 0.0767 |

b) Preparation of Suspensions/Solutions and Analysis of pH and Solubility

Procedure: The corresponding amount of water and the respective equivalents of 1 M aqueous NaOH was added to each sample. The suspensions were stirred at room temperature, at 40° C. or at 60° C. respectively. The pH, solubility and precipitation were monitored at 12 h, 24 h, 48 h and 7 days (Table 11, Table 12, Table 13 and Table 14)

TABLE 11

Preparation of samples of letermovir free base of 20 mg/mL in water with different equivalents of NaOH at room temperature.

| Letermovir Free Base concentration [mg/ml] | NaOH/Letermovir Molar Ratio | μL of 1M $NaOH_{aq}$ | mL of $H_2O$ | pH 12 h | pH 24 h | pH 48 h | pH 1 w | Solubility |
|---|---|---|---|---|---|---|---|---|
| 20 | 0.80/1 | 107 | 3.72 | 7.7 | 7.7 | 7.7 | 7.7 | a |
| 20 | 0.82/1 | 108 | 3.68 | 7.7 | 7.7 | 7.7 | 7.7 | a |
| 20 | 0.84/1 | 112 | 3.69 | 7.7 | 7.7 | 7.7 | 7.7 | b |
| 20 | 0.86/1 | 116 | 3.74 | 7.7 | 7.7 | 7.7 | 7.7 | c |
| 20 | 0.88/1 | 119 | 3.74 | 7.9 | 7.8 | 7.8 | 7.8 | c |
| 20 | 0.90/1 | 122 | 3.75 | 8.2 | 7.9 | 7.9 | 7.9 | c |
| 20 | 1/1 | 134 | 3.69 | 8.7 | 8.5 | 8.5 | 8.5 | c |

a: particles in suspension;
b: particles in suspension, but after 24 h only above the solution (interphase air-water);
c: few particles in suspension, but after 24 h only above the solution (interphase air-water).

TABLE 12

Preparation of samples of letermovir free base of 100 mg/mL in water with different equivalents of NaOH at room temperature.

| Letermovir Free Base concentration [mg/ml] | NaOH/Letermovir Molar Ratio | μL of 1M $NaOH_{aq}$ | mL of $H_2O$ | pH 12 h | pH 24 h | pH 48 h | pH 1 w | Solubility |
|---|---|---|---|---|---|---|---|---|
| 100 | 0.80/1 | 409 | 2.52 | 7.4 | 7.5 | 7.5 | 7.5 | b |
| 100 | 0.82/1 | 420 | 2.51 | 7.5 | 7.5 | 7.5 | 7.5 | b |
| 100 | 0.84/1 | 429 | 2.50 | 7.6 | 7.6 | 7.6 | 7.6 | b |
| 100 | 0.86/1 | 439 | 2.48 | 7.6 | 7.6 | 7.6 | 7.6 | c |
| 100 | 0.88/1 | 451 | 2.48 | 7.7 | 7.7 | 7.7 | 7.7 | c |
| 100 | 0.90/1 | 462 | 2.48 | 7.8 | 7.7 | 7.7 | 7.7 | c |
| 100 | 1/1 | 514 | 2.43 | 8.6 | 8.5 | 8.5 | 8.4 | c |

b: particles in suspension, but after 24 h only above the solution (interphase air-water);
c: few particles in suspension, but after 24 h only above the solution (interphase air-water).

TABLE 13

Preparation of samples of letermovir free base of 20 mg/mL in water with different equivalents of NaOH at 40° C. and 60° C.

| Letermovir Free Base concentration [mg/ml] | Temperature | NaOH/Letermovir Molar Ratio | μL of 1M $NaOH_{aq}$ | mL of $H_2O$ | pH 12 h | pH 24 h | pH 48 h | pH 1 w | Solubility |
|---|---|---|---|---|---|---|---|---|---|
| 20 | 40° C. | 0.84/1 | 113 | 3.72 | 7.5 | 7.4 | 7.5 | 7.5 | d |
| 20 | 40° C. | 0.86/1 | 117 | 3.79 | 7.6 | 7.5 | 7.6 | 7.6 | e |
| 20 | 40° C. | 0.88/1 | 119 | 3.76 | 7.7 | 7.6 | 7.6 | 7.7 | f |
| 20 | 60° C. | 0.84/1 | 114 | 3.77 | 7.5 | 7.4 | 7.3 | 7.4 | g |
| 20 | 60° C. | 0.86/1 | 115 | 3.72 | 7.5 | 7.4 | 7.4 | 7.5 | h |
| 20 | 60° C. | 0.88/1 | 120 | 3.78 | 7.6 | 7.5 | 7.5 | 7.6 | i |

d: some particles in suspension, even after 1 week;
e: some particles in suspension, after 24 h few particles, after 48 h only above the solution and after 1 week, clear solution;
f: few particles in suspension, after 24 h only above the solution and after 1 week, clear solution;
g: cloudy;
h: few particles in suspension, even after 1 week;
i: clear solution.

TABLE 14

Preparation of samples of letermovir free base of 100 mg/mL in water with different equivalents of NaOH at 40° C. and 60° C.

| Letermovir Free Base concentration [mg/ml] | Temperature | NaOH/Letermovir Molar Ratio | μL of 1M $NaOH_{aq}$ | mL of $H_2O$ | pH 12 h | pH 24 h | pH 48 h | pH 1 w | Solubility |
|---|---|---|---|---|---|---|---|---|---|
| 100 | 40° C. | 0.84/1 | 431 | 2.51 | 7.5 | 7.5 | 7.5 | 7.5 | j |
| 100 | 40° C. | 0.86/1 | 440 | 2.49 | 7.5 | 7.5 | 7.5 | 7.5 | c |
| 100 | 40° C. | 0.88/1 | 452 | 2.49 | 7.5 | 7.5 | 7.5 | 7.5 | c |
| 100 | 60° C. | 0.84/1 | 430 | 2.50 | 7.4 | 7.4 | 7.4 | 7.4 | k |

TABLE 14-continued

| Preparation of samples of letermovir free base of 100 mg/mL in water with different equivalents of NaOH at 40° C. and 60° C. | | | | | | | | | |
|---|---|---|---|---|---|---|---|---|---|
| Letermovir Free Base concentration [mg/ml] | Temperature | NaOH/Letermovir Molar Ratio | μL of 1M $NaOH_{aq}$ | mL of $H_2O$ | pH 12 h | pH 24 h | pH 48 h | pH 1 w | Solubility |
| 100 | 60° C. | 0.86/1 | 441 | 2.50 | 7.4 | 7.4 | 7.5 | 7.5 | k |
| 100 | 60° C. | 0.88/1 | 453 | 2.49 | 7.5 | 7.5 | 7.6 | 7.6 | k |

c: few particles in suspension, but after 24 h only above the solution;
j: few particles in suspension, after 24 h, clear solution;
k: clear coloured solution.

Results

The 100 mg/mL samples kept at 60° C. resulted in clear colored solutions as determined by visual inspection, which were further analysed by HPLC. No additional signals were observed. 20 μL of sample were diluted with 1 mL of water in order to achieve the concentration of 2 mg/mL prior to HPLC analysis.

Samples of 20 mg/mL of letermovir free base with 0.8 and 0.82 equivalents of sodium hydroxide contained particles in the suspension. An increase in the solubility was observed when the amount of equivalents of sodium hydroxide increased, and after 2 h the samples were almost completely dissolved (only some particles were observed in the air-water interphase).

All the samples of 100 mg/mL of letermovir free base were almost completely dissolved (only some particles were observed in the air-water interphase).

By increasing the temperature, the following effects were observed:

40° C.

- Sample of 20 mg/mL of letermovir free base with 0.84 equivalents of NaOH contained particles in the suspension.
- Samples of 20 and 100 mg/mL of letermovir free base with 0.86 and 0.88 equivalents of NaOH were clear solutions after 1 week.
- Sample of 100 mg/mL of letermovir free base with 0.84 equivalents of NaOH was a clear solution after 1 week.

60° C.

- Sample of 20 mg/mL of letermovir free base with 0.84 equivalents of NaOH was a cloudy suspension.
- Sample of 20 mg/mL of letermovir free base with 0.86 equivalents of NaOH contained particles in suspension even after 1 week.
- Sample of 20 mg/mL of letermovir free base with 0.88 equivalents of NaOH was a clear solution after 1 week.
- Samples of 100 mg/mL of letermovir free base with 0.84, 0.86 and 0.88 equivalents of NaOH were clear but colored solutions after 1 week.

Example 3. Lyophilization after 7 Days and Reconstitution in Water a) Initial Drying 14 samples of letermovir free base were prepared by weighing the substance and drying in a vacuum oven at 90° C. (ca. 5 mbar) overnight in order to remove residual water and to avoid weighing errors to calculate the equivalents of NaOH (Table 15).

Samples of ca. 80 mg and 300 mg were weighed to be dissolved in 4 mL and 3 mL, respectively, to prepare 20 mg/mL and 100 mg/mL solutions.

TABLE 15

| Initial drying process of 14 samples of letermovir free base. | | | | |
|---|---|---|---|---|
| Planned Letermovir Free Base Concentration [mg/ml] | Planned NaOH/Letermovir Molar Ratio | Starting material, g | Sample lost, g | Final weight, g |
| 20 | 0.80/1 | 0.0811 | 0.0044 | 0.0767 |
| 20 | 0.82/1 | 0.0811 | 0.0037 | 0.0774 |
| 20 | 0.84/1 | 0.0811 | 0.0040 | 0.0771 |
| 20 | 0.86/1 | 0.0811 | 0.0035 | 0.0776 |
| 20 | 0.88/1 | 0.0805 | 0.0035 | 0.0770 |
| 20 | 0.90/1 | 0.0807 | 0.0041 | 0.0766 |
| 20 | 1/1 | 0.0813 | 0.0038 | 0.0775 |
| 100 | 0.80/1 | 0.3008 | 0.0079 | 0.2929 |
| 100 | 0.82/1 | 0.3015 | 0.0079 | 0.2936 |
| 100 | 0.84/1 | 0.3002 | 0.008 | 0.2922 |
| 100 | 0.86/1 | 0.3005 | 0.0082 | 0.2923 |
| 100 | 0.88/1 | 0.3009 | 0.008 | 0.2929 |
| 100 | 0.90/1 | 0.3001 | 0.0079 | 0.2922 |
| 100 | 1/1 | 0.3009 | 0.0088 | 0.2921 |

b) Preparation of Suspensions/Solutions and Analysis of Solubility

Procedure: The corresponding amount of water and the respective equivalents of 1 M aqueous NaOH were added to each sample. The suspensions were stirred at room temperature and the solubility and precipitation effects were checked (Table 16).

TABLE 16

| Preparation of samples of letermovir free base in water and with different equivalents of NaOH. | | | |
|---|---|---|---|
| Letermovir Free Base Concentration [mg/ml] | NaOH/Letermovir Molar Ratio | μL of 1M $NaOH_{aq}$ | mL of $H_2O$ |
| 20 | 0.80/1 | 107 | 3.73 |
| 20 | 0.82/1 | 111 | 3.76 |
| 20 | 0.84/1 | 113 | 3.74 |
| 20 | 0.86/1 | 117 | 3.76 |
| 20 | 0.88/1 | 118 | 3.73 |
| 20 | 0.90/1 | 120 | 3.71 |
| 20 | 1/1 | 135 | 3.74 |
| 100 | 0.80/1 | 409 | 2.52 |
| 100 | 0.82/1 | 420 | 2.52 |
| 100 | 0.84/1 | 429 | 2.49 |
| 100 | 0.86/1 | 439 | 2.48 |
| 100 | 0.88/1 | 450 | 2.48 |
| 100 | 0.90/1 | 459 | 2.46 |
| 100 | 1/1 | 510 | 2.41 |

Solubility Over 7 Days

After 24 h there was still some precipitate in all samples. After 48 h the precipitate remained in the samples of 20 mg/mL with 0.8 and 0.82 equivalents of NaOH. In the other samples only a small amount of solid was observed on the air-water interphase.

After 1 week the precipitate remained in the samples of 20 mg/mL with 0.8 and 0.82 equivalents of NaOH. In the sample of 20 mg/ml with 0.84 equivalents of NaOH a small amount of solid was observed on the air-water interphase.

The rest of the samples were clear solutions after a week as determined by visual inspection.

c) Lyophilisation and Reconstitution in Water

After 1 week the samples were lyophilised.

Procedure:

Samples of 20 mg/mL: an aliquot of 3 ml, was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 3 ml, of water in order to get a final concentration of 20 mg/mL and checked for precipitation and pH (Table 17).

Samples of 100 mg/mL: an aliquot of 2.6 ml was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 13 ml of water in order to get a final concentration of 20 mg/mL and checked for precipitation and pH (Table 17).

TABLE 17

Lyophilization and reconstitution in water

| Initial Letermovir Free Base Concentration [mg/ml] | Initial NaOH/Letermovir Molar Ratio | Final concentration [mg/ml] | pH | Solubility |
|---|---|---|---|---|
| 20 | 0.80/1 | 20 | 7.6 | Clear solution |
| 20 | 0.82/1 | 20 | 7.6 | Clear solution |
| 20 | 0.84/1 | 20 | 7.7 | Clear solution |
| 20 | 0.86/1 | 20 | 7.7 | Clear solution |
| 20 | 0.88/1 | 20 | 7.8 | Clear solution |
| 20 | 0.90/1 | 20 | 7.8 | Clear solution |
| 20 | 1/1 | 20 | 8.2 | Clear solution |
| 100 | 0.80/1 | 20 | 7.6 | Clear solution |
| 100 | 0.82/1 | 20 | 7.6 | Clear solution |
| 100 | 0.84/1 | 20 | 7.7 | Clear solution |
| 100 | 0.86/1 | 20 | 7.7 | Clear solution |
| 100 | 0.88/1 | 20 | 7.8 | Clear solution |
| 100 | 0.90/1 | 20 | 7.8 | Clear solution |
| 100 | 1/1 | 20 | 8.2 | Clear solution |

Example 4. Lyophilization after 7 Days and Reconstitution in Ringer's Lactate Solution a) Initial Drying 14 samples of letermovir free base were prepared by weighing the substance and drying in a vacuum oven at 90° C. (ca. 5 mbar) overnight in order to remove residual water and to avoid weighing errors to calculate the equivalents of NaOH (Table 18).

Samples of ca. 80 mg and 300 mg were weighed to be dissolved in 4 ml, and 3 mL, respectively, to prepare 20 mg/mL and 100 mg/mL solutions.

TABLE 18

Initial drying process of 14 samples of letermovir Free Base.

| Planned Letermovir Free Base Concentration [mg/ml] | Planned NaOH/Letermovir Molar Ratio | Starting material, g | Sample lost, g | Final weight, g |
|---|---|---|---|---|
| 20 | 0.80/1 | 0.0810 | 0.0043 | 0.0767 |
| 20 | 0.82/1 | 0.0806 | 0.0038 | 0.0768 |
| 20 | 0.84/1 | 0.0802 | 0.0044 | 0.0758 |
| 20 | 0.86/1 | 0.0809 | 0.0045 | 0.0764 |
| 20 | 0.88/1 | 0.0813 | 0.0046 | 0.0767 |
| 20 | 0.90/1 | 0.0804 | 0.0047 | 0.0757 |
| 20 | 1/1 | 0.0806 | 0.006 | 0.0746 |
| 100 | 0.80/1 | 0.3006 | 0.0087 | 0.2919 |
| 100 | 0.82/1 | 0.3014 | 0.0104 | 0.2910 |
| 100 | 0.84/1 | 0.3018 | 0.0098 | 0.2920 |
| 100 | 0.86/1 | 0.3015 | 0.0083 | 0.2932 |
| 100 | 0.88/1 | 0.3022 | 0.0089 | 0.2933 |
| 100 | 0.90/1 | 0.3019 | 0.0106 | 0.2913 |
| 100 | 1/1 | 0.3023 | 0.0088 | 0.2935 |

b) Preparation of Suspensions/Solutions and Analysis of Solubility

Procedure: The corresponding amount of water and the respective equivalents of 1 M aqueous NaOH were added to each sample. The suspensions were stirred at room temperature and the solubility and precipitation effects were checked (Table 19).

TABLE 19

Preparation of samples of letermovir free base in water and with different equivalents of NaOH.

| Letermovir Free Base Concentration [mg/ml] | NaOH/Letermovir Molar Ratio | μL of 1M $NaOH_{aq}$ | mL of $H_2O$ |
|---|---|---|---|
| 20 | 0.80/1 | 107 | 3.73 |
| 20 | 0.82/1 | 110 | 3.73 |
| 20 | 0.84/1 | 111 | 3.68 |
| 20 | 0.86/1 | 115 | 3.71 |
| 20 | 0.88/1 | 118 | 3.72 |
| 20 | 0.90/1 | 119 | 3.67 |
| 20 | 1/1 | 130 | 3.60 |
| 100 | 0.80/1 | 408 | 2.51 |
| 100 | 0.82/1 | 417 | 2.49 |
| 100 | 0.84/1 | 428 | 2.49 |
| 100 | 0.86/1 | 440 | 2.49 |
| 100 | 0.88/1 | 451 | 2.48 |
| 100 | 0.90/1 | 458 | 2.46 |
| 100 | 1/1 | 513 | 2.42 |

Solubility Over 7 Days

After 24 h there was still some precipitate in all the samples. After 48 h the precipitate remained in the samples of 20 mg/mL with 0.8 and 0.82 equivalents of NaOH. In the other samples only a small amount of solid was observed on the air-water interphase.

After 1 week the precipitate remained in the samples of 20 mg/mL with 0.8 and 0.82 equivalents of NaOH. In the sample of 20 mg/ml with 0.84 equivalents of NaOH a small amount of solid was observed on the air-water interphase.

The other samples were clear solutions after a week as determined by visual inspection.

c) Lyophilisation and Reconstitution in Ringer's Lactate

After 1 week the samples were lyophilised.

Procedure:

Samples of 20 mg/mL: an aliquot of 3 mL was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 3 mL of Ringer's Lactate solution in order to get a final concentration of 20 mg/mL and checked for precipitation and pH (Table 20).

Samples of 100 mg/mL: an aliquot of 2.6 mL was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 13 mL of Ringer's Lactate solution in order to get a final concentration of 20 mg/mL and checked for precipitation and pH (Table 20).

TABLE 20

Lyophilization and reconstitution in Ringer's Lactate.

| Initial Letermovir Free Base Concentration [mg/ml] | Initial NaOH/Letermovir Molar Ratio | Final concentration [mg/ml] | pH | Solubility |
|---|---|---|---|---|
| 20 | 0.80/1 | 20 | 7.4 | Some particles After 2 h, clear solution |
| 20 | 0.82/1 | 20 | 7.4 | Some particles After 2 h, clear solution |
| 20 | 0.84/1 | 20 | 7.4 | Clear solution |
| 20 | 0.86/1 | 20 | 7.4 | Clear solution |
| 20 | 0.88/1 | 20 | 7.5 | Clear solution |
| 20 | 0.90/1 | 20 | 7.6 | Clear solution |
| 20 | 1/1 | 20 | 7.7 | Clear solution |
| 100 | 0.80/1 | 20 | 7.4 | Clear solution |
| 100 | 0.82/1 | 20 | 7.4 | Clear solution |
| 100 | 0.84/1 | 20 | 7.4 | Clear solution |
| 100 | 0.86/1 | 20 | 7.5 | Clear solution |
| 100 | 0.88/1 | 20 | 7.6 | Clear solution |
| 100 | 0.90/1 | 20 | 7.6 | Clear solution |
| 100 | 1/1 | 20 | 7.9 | Clear solution |

Example 5. Lyophilization after 7 Days and Reconstitution in Glucose Aqueous 5% Solution a) Initial Drying 14 samples of letermovir free base were prepared by weighing the substance and drying in a vacuum oven at 90° C. (ca. 5 mbar) overnight in order to remove residual water and to avoid weighing errors to calculate the equivalents of NaOH (Table 21).

Samples of ca. 80 mg and 300 mg were weighed to be dissolved in 4 mL and 3 mL, respectively, to prepare 20 mg/mL and 100 mg/mL solutions.

TABLE 21

Initial drying process of 14 samples of letermovir free base.

| Planned Letermovir Free Base Concentration [mg/ml] | Planned NaOH/Letermovir Molar Ratio | Starting material, g | Sample lost, g | Final weight, g |
|---|---|---|---|---|
| 20 | 0.80/1 | 0.0804 | 0.0051 | 0.0753 |
| 20 | 0.82/1 | 0.0803 | 0.0056 | 0.0747 |
| 20 | 0.84/1 | 0.0814 | 0.004 | 0.0774 |
| 20 | 0.86/1 | 0.0804 | 0.0043 | 0.0761 |
| 20 | 0.88/1 | 0.0814 | 0.0054 | 0.0760 |
| 20 | 0.90/1 | 0.0812 | 0.0041 | 0.0771 |
| 20 | 1/1 | 0.0804 | 0.0061 | 0.0743 |
| 100 | 0.80/1 | 0.3025 | 0.0084 | 0.2941 |
| 100 | 0.82/1 | 0.3018 | 0.0086 | 0.2932 |
| 100 | 0.84/1 | 0.3023 | 0.0077 | 0.2946 |
| 100 | 0.86/1 | 0.3015 | 0.0077 | 0.2938 |
| 100 | 0.88/1 | 0.3021 | 0.0094 | 0.2927 |
| 100 | 0.90/1 | 0.3012 | 0.0085 | 0.2927 |
| 100 | 1/1 | 0.3016 | 0.0085 | 0.2931 |

b) Preparation of Suspensions/Solutions and Analysis of Solubility

Procedure: the corresponding amount of water and the respective equivalents of 1 M aqueous NaOH were added to each sample. The suspensions were stirred at room temperature and the solubility and precipitation effects were checked (Table 22).

TABLE 22

Preparation of samples of letermovir free base in water and with different equivalents of NaOH.

| Letermovir Free Base Concentration [mg/ml] | NaOH/Letermovir Molar Ratio | μL of 1M $NaOH_{aq}$ | mL of $H_2O$ |
|---|---|---|---|
| 20 | 0.80/1 | 105 | 3.66 |
| 20 | 0.82/1 | 107 | 3.63 |
| 20 | 0.84/1 | 114 | 3.76 |
| 20 | 0.86/1 | 114 | 3.69 |
| 20 | 0.88/1 | 117 | 3.68 |
| 20 | 0.90/1 | 121 | 3.73 |
| 20 | 1/1 | 130 | 3.59 |
| 100 | 0.80/1 | 411 | 2.53 |
| 100 | 0.82/1 | 420 | 2.51 |
| 100 | 0.84/1 | 432 | 2.51 |
| 100 | 0.86/1 | 441 | 2.50 |
| 100 | 0.88/1 | 450 | 2.48 |
| 100 | 0.90/1 | 460 | 2.47 |
| 100 | 1/1 | 512 | 2.42 |

Solubility Over 7 Days

After 24 h there was still some precipitate in all the samples. After 48 h the precipitate remained in the samples of 20 mg/mL with 0.8 and 0.82 equivalents of NaOH. In the other samples only a small amount of solid was observed on the air-water interphase.

After 1 week the precipitate remained in the samples of 20 mg/mL with 0.8 and 0.82 equivalents of NaOH. In the sample of 20 mg/ml with 0.84 equivalents of NaOH a small amount of solid was observed only on the air-water interphase.

The other samples were clear solutions after a week as determined by visual inspection.

c) Lyophilisation and Reconstitution in Glucose 5% Aqueous Solution

After 1 week the samples were lyophilised.

Procedure:

Samples of 20 mg/mL: an aliquot of 3 ml, was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 3 ml of a 5% glucose solution in order to get a final concentration of 20 mg/ml and checked for precipitation and pH (Table 23).

Samples of 100 mg/mL: an aliquot of 2.6 ml, was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 13 mL of a 5% glucose solution in order to get a final concentration of 100 mg/mL and checked for precipitation and pH (Table 23).

TABLE 23

Lyophilization and reconstitution in glucose 5% aqueous solution.

| Letermovir Free Base Initial Concentration [mg/ml] | Initial NaOH/Letermovir Molar Ratio | Final concentration [mg/ml] | pH | Solubility |
|---|---|---|---|---|
| 20 | 0.80/1 | 20 | 7.5 | Cloudy |
| 20 | 0.82/1 | 20 | 7.5 | Cloudy |
| 20 | 0.84/1 | 20 | 7.5 | Clear solution |
| 20 | 0.88/1 | 20 | 7.6 | Clear solution |
| 20 | 0.90/1 | 20 | 7.7 | Clear solution |
| 100 | 0.80/1 | 20 | 7.5 | Clear solution |
| 100 | 0.82/1 | 20 | 7.6 | Clear solution |
| 100 | 0.84/1 | 20 | 7.6 | Clear solution |
| 100 | 0.86/1 | 20 | 7.7 | Clear solution |
| 100 | 0.90/1 | 20 | 7.8 | Clear solution |
| 100 | 1/1 | 20 | 8.2 | Clear solution |

SUMMARY

Samples that were lyophilised (from initial concentrations of 20 and 100 mg/mL) were completely dissolved in the reconstitution in water and Ringer's Lactate solution at 20 mg/mL. When Glucose 5% solution was employed, samples from an initial concentration of 20 mg/mL and 0.8 or 0.82 equivalents of NaOH provided cloudy suspensions.

Example 6. Study of the Solubility and pH of Letermovir Letermovir Free Base with NaOH Equivalents from 0.6 to 0.78 with Respect to Letermovir Free Base A set of samples was prepared by adding different molar equivalents of sodium hydroxide (0.60, 0.62, 0.64, 0.66, 0.68, 0.70, 0.72, 0.74, 0.76, 0.78) to letermovir free base solutions. Letermovir free base was dried in a vacuum oven at 90° C. (ca. 5 mbar) overnight to remove residual water.

a) Initial Drying

Procedure: 22 samples of letermovir free base were prepared by weighing the corresponding substance and drying in a vacuum oven at 90° C. (ca. 5 mbar) overnight to remove residual water and to avoid weighing errors to calculate the equivalents of NaOH (Table 24).

Samples of letermovir free base were weighed to be dissolved in 7.5 mL and 5 mL, respectively, to prepare solutions with concentrations of 20 mg/mL and 100 mg/mL with respect to letermovir free base.

TABLE 24

Initial drying of 22 samples of letermovir free base

| Letermovir form | Starting material, g | Sample lost, g | Sample lost (%) | Final weight, g |
|---|---|---|---|---|
| Free Base | 0.1523 | 0.0065 | 4.3 | 0.1458 |
| Free Base | 0.1588 | 0.005 | 3.1 | 0.1538 |
| Free Base | 0.1598 | 0.004 | 2.5 | 0.1558 |
| Free Base | 0.1579 | 0.0064 | 4.1 | 0.1515 |
| Free Base | 0.1535 | 0.0039 | 2.5 | 0.1496 |
| Free Base | 0.1589 | 0.0041 | 2.6 | 0.1548 |
| Free Base | 0.1571 | 0.004 | 2.5 | 0.1531 |
| Free Base | 0.152 | 0.0061 | 4.0 | 0.1459 |
| Free Base | 0.1578 | 0.0046 | 2.9 | 0.1532 |
| Free Base | 0.1547 | 0.0052 | 3.4 | 0.1495 |
| Free Base | 0.1576 | 0.0044 | 2.8 | 0.1532 |
| Free Base | 0.518 | 0.0112 | 2.2 | 0.5068 |
| Free Base | 0.5134 | 0.014 | 2.7 | 0.4994 |
| Free Base | 0.513 | 0.0117 | 2.3 | 0.5013 |
| Free Base | 0.5194 | 0.0118 | 2.3 | 0.5076 |
| Free Base | 0.5137 | 0.0108 | 2.1 | 0.5029 |
| Free Base | 0.5162 | 0.0123 | 2.4 | 0.5039 |
| Free Base | 0.5133 | 0.0121 | 2.4 | 0.5012 |
| Free Base | 0.5117 | 0.0119 | 2.3 | 0.4998 |
| Free Base | 0.5139 | 0.0112 | 2.2 | 0.5027 |
| Free Base | 0.5152 | 0.0147 | 2.9 | 0.5005 |
| Free Base | 0.5131 | 0.0123 | 2.4 | 0.5008 |

b) Preparation of Suspensions/Solutions and Analysis of DpH and Solubility

Procedure: A solution of NaOH 1N standard and water was prepared (end volume 7.5 and 5 mL). The alkalified solution was added to the solid. The suspensions were stirred at room temperature until complete dissolution of the solid. The samples were filled up with water to the target volume of 7.5 and 5 mL achieving the desired concentration of 20 or 100 mg/mL, respectively. The suspensions were stirred at room temperature and pH, solubility and precipitation were monitored after 24 h, 48 h and 7 days. Temperature analysis was taken into consideration determining environmental temperature vs solution temperature after 12 h, 24 h, 48 h and 7 days.

TABLE 25

Analysis of pH and solubilities (concentration of letermovir free base of 20 mg/ml).

| Letermovir Free Base concentration [mg/ml]/ NaOH/Letermovir | 24 hours | | | 48 hours | | | 7 days | | |
|---|---|---|---|---|---|---|---|---|---|
| Molar Ratio / | pH | Solubility | $T_{out}$ vs $T_{in}$ (° C.) | pH | Solubility | $T_{out}$ vs $T_{in}$ (° C.) | pH | Solubility | $T_{out}$ vs $T_{in}$ (° C.) |
| 20/0.60 | 7.7 | White suspension | 24.5 vs 24.1 | 7.7 | White suspension | 24.4 vs 24.1 | 7.8 | White suspension | 23.0 vs 23.0 |
| 20/0.62 | 7.4 | White suspension | 24.5 vs 24.1 | 7.4 | White suspension | 24.4 vs 24.2 | 7.4 | White suspension | 23.0 vs 22.9 |

TABLE 25-continued

Analysis of pH and solubilities (concentration of letermovir free base of 20 mg/ml).

| Letermovir Free Base concentration [mg/ml]/ NaOH/Letermovir Molar Ratio / | 24 hours | | | 48 hours | | | 7 days | | |
|---|---|---|---|---|---|---|---|---|---|
| | pH | Solubility | $T_{out}$ vs $T_{in}$ (° C.) | pH | Solubility | $T_{out}$ vs $T_{in}$ (° C.) | pH | Solubility | $T_{out}$ vs $T_{in}$ (° C.) |
| 20/0.64 | 7.6 | White suspension | 24.5 vs 24.1 | 7.6 | White suspension | 24.4 vs 24.1 | 7.6 | White suspension | 23.1 vs 23.1 |
| 20/0.66 | 7.5 | White suspension | 24.5 vs 24.1 | 7.6 | Cloudy | 24.4 vs 24.1 | 7.6 | Cloudy | 23.1 vs 23.1 |
| 20/0.68 | 7.6 | Cloudy | 24.5 vs 24.1 | 7.5 | Cloudy | 24.4 vs 24.2 | 7.7 | Cloudy | 23.2 vs 23.2 |
| 20/0.70 | 7.5 | Cloudy | 24.6 vs 24.1 | 7.5 | Cloudy | 24.4 vs 24.1 | 7.6 | White suspension | 23.2 vs 23.2 |
| 20/0.72 | 7.5 | Cloudy | 24.6 vs 24.2 | 7.5 | Cloudy | 24.4 vs 24.2 | 7.7 | Cloudy | 23.2 vs 23.2 |
| 20/0.74 | 7.5 | Cloudy | 24.5 vs 24.2 | 7.6 | Cloudy | 24.4 vs 24.3 | 7.6 | Cloudy | 23.2 vs 23.1 |
| 20/0.76 | 7.5 | Cloudy | 24.6 vs 24.2 | 7.6 | Cloudy | 24.4 vs 24.3 | 7.7 | Cloudy | 23.1 vs 23.0 |
| 20/0.78 | 7.5 | Many particles in suspension | 24.6 vs 24.2 | 7.5 | Many particles in suspension | 24.4 vs 24.3 | 7.7 | Many particles in suspension | 23.1 vs 23.1 |

TABLE 26

Analysis of pH and solubilities (concentration of letermovir free base of 100 mg/ml).

| Letermovir Free Base concentration [mg/ml]/ NaOH/Letermovir Molar Ratio / | 24 hours | | | 48 hours | | | 7 days | | |
|---|---|---|---|---|---|---|---|---|---|
| | pH | Solubility | $T_{out}$ vs $T_{in}$ (° C.) | pH | Solubility | $T_{out}$ vs $T_{in}$ (° C.) | pH | Solubility | $T_{out}$ vs $T_{in}$ (° C.) |
| 100/0.60 | 7.4 | White suspension | 24.7 vs 24.2 | 7.5 | White suspension | 24.6 vs 24.3 | 7.4 | White suspension | 23.2 vs 23.2 |
| 100/0.62 | 7.4 | White suspension | 24.7 vs 24.2 | 7.3 | White suspension | 24.6 vs 24.5 | 7.4 | White suspension | 23.2 vs 23.1 |
| 100/0.64 | 7.4 | White suspension | 24.7 vs 24.2 | 7.4 | White suspension | 24.6 vs 24.5 | 7.4 | White suspension | 23.2 vs 23.1 |
| 100/0.66 | 7.3 | White suspension | 24.7 vs 24.2 | 7.4 | White suspension | 24.6 vs 24.5 | 7.4 | White suspension | 23.2 vs 23.1 |
| 100/0.68 | 7.4 | White suspension | 24.7 vs 24.2 | 7.4 | White suspension | 24.6 vs 24.5 | 7.4 | White suspension | 23.2 vs 23.2 |
| 100/0.70 | 7.4 | Cloudy | 24.7 vs 24.2 | 7.4 | Cloudy | 24.6 vs 24.5 | 7.4 | Some particles in suspension | 23.2 vs 23.3 |
| 100/0.72 | 7.3 | Few particles in suspension | 24.7 vs 24.2 | 7.3 | Few particles in suspension | 24.6 vs 24.5 | 7.4 | Very few particles in suspension | 23.2 vs 23.3 |
| 100/0.74 | 7.4 | Very few particles in suspension | 24.7 vs 24.2 | 7.4 | Very few particles in suspension | 24.6 vs 24.5 | 7.4 | Clear solution | 23.2 vs 23.3 |
| 100/0.76 | 7.4 | Some particles in suspension | 24.7 vs 24.2 | 7.4 | Few particles in suspension | 24.5 vs 24.5 | 7.4 | Clear solution | 23.3 vs 23.3 |
| 100/0.78 | 7.4 | Very few particles in suspension | 24.6 vs 24.3 | 7.4 | Clear solution | 24.5 vs 24.5 | 7.5 | Clear solution | 23.3 vs 23.4 |

Lyophilisation and Reconstitution in Water

Procedure:

Samples of 20 mg/mL: an aliquot of 2 mL was placed in the freezer for 2 hours. The samples were frozen using liquid nitrogen and the freeze drying process was performed over 2 days (average vacuum ca. 0.05 mbar, temperature ca. −86° C.).

A white amorphous powder was obtained. The obtained solid was analysed by PXRD which confirmed the amorphous nature of the freeze-dried material. The obtained solid was solubilized with ca. 2 mL of water to a final concentration of 20 mg/mL and checked for precipitation and pH.

Samples of 100 mg/mL: an aliquot of 1.5 mL was placed in the freezer for 2 hours. The samples were frozen using liquid nitrogen and the freeze drying process was performed over 2 days (average vacuum ca. 0.05 mbar, temperature ca. −86° C.). A white amorphous powder was obtained. The obtained solid was analysed by PXRD which confirmed the amorphous nature of the freeze-dried material. The obtained solid was solubilized with ca. 7.5 mL of water to a final concentration of 100 mg/mL and checked for precipitation and pH.

TABLE 27

Reconstitution in water (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 20/0.6 | Amorphous | 7.5 | White suspension |
| 20/0.62 | Amorphous | 7.5 | White suspension |
| 20/0.64 | Amorphous | 7.6 | White suspension |
| 20/0.66 | Amorphous | 7.6 | White suspension |
| 20/0.68 | Amorphous | 7.7 | White suspension |
| 20/0.70 | Amorphous | 7.8 | White suspension |
| 20/0.72 | Amorphous | 7.7 | White suspension |

TABLE 27-continued

Reconstitution in water (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 20/0.74 | Amorphous | 7,7 | Cloudy |
| 20/0.76 | Amorphous | 7.7 | Cloudy |
| 20/0.78 | Amorphous | 7.7 | Cloudy |

TABLE 28

Reconstitution in water (concentration of letermovir free base of 100 mg/ml).

| Letermovir Free Base concentration [mg/ml]/ NaOH/Letermovir Molar Ratio | PXRD | pH | Precipitation/ solubility |
|---|---|---|---|
| 100/0.6 | Amorphous | 7.7 | White suspension |
| 100/0.62 | Amorphous | 7.7 | White suspension |
| 100/0.64 | Amorphous | 7.7 | White suspension |
| 100/0.66 | Amorphous | 7.7 | White suspension |
| 100/0.68 | Amorphous | 7.7 | White suspension |
| 100/0.70 | Amorphous | 7.7 | White suspension |
| 100/0.72 | Amorphous | 7.7 | White suspension |
| 100/0.74 | Amorphous | 7.7 | White suspension |
| 100/0.76 | Amorphous | 7.7 | White suspension |
| 100/0.78 | Amorphous | 7.7 | White suspension |

Lyophilisation and Reconstitution in Glucose 5% Solution in Water

Procedure:

Samples of 20 mg/mL: an aliquot of 2 mL was placed in the freezer for 2 hours. The samples were frozen using liquid nitrogen and the freeze-drying process was performed over 2 days (average vacuum ca. 0.05 mbar, temperature ca. −86° C.).

A white amorphous powder was obtained. The obtained solid was analysed by PXRD which confirmed the amorphous nature of the freeze-dried material. The obtained solid was solubilized with ca. 2 mL of glucose 5% w/v solution in water to a final concentration of 20 mg/mL and checked for precipitation and pH.

Samples of 100 mg/mL: an aliquot of 1.5 mL was placed in the freezer for 2 hours. The samples were frozen using liquid nitrogen and the freeze-drying process was performed over 2 days (average vacuum ca. 0.05 mbar, temperature ca. −86° C.).

A white amorphous powder was obtained. The obtained solid was analysed by PXRD which confirmed the amorphous nature of the freeze-dried material. The obtained solid was solubilized with ca. 7.5 mL of glucose 5% w/v solution in water to a final concentration of 100 mg/mL and checked for precipitation and pH.

TABLE 29

Reconstitution in glucose 5% aqueous solution (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 20/0.6 | Amorphous | 7.6 | White suspension |
| 20/0.62 | Amorphous | 7.6 | White suspension |
| 20/0.64 | Amorphous | 7.6 | White suspension |
| 20/0.66 | Amorphous | 7.6 | White suspension |
| 20/0.68 | Amorphous | 7.6 | White suspension |
| 20/0.70 | Amorphous | 7.6 | White suspension |
| 20/0.72 | Amorphous | 7.7 | White suspension |
| 20/0.74 | Amorphous | 7.6 | White suspension |
| 20/0.76 | Amorphous | 7.6 | Cloudy |
| 20/0.78 | Amorphous | 7.6 | Cloudy |

TABLE 30

Reconstitution in glucose 5% aqueous solution (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 100/0.6 | Amorphous | 7.7 | White suspension |
| 100/0.62 | Amorphous | 7.8 | White suspension |
| 100/0.64 | Amorphous | 7.8 | White suspension |
| 100/0.66 | Amorphous | 7.7 | White suspension |
| 100/0.68 | Amorphous | 7.7 | White suspension |
| 100/0.70 | Amorphous | 7.7 | White suspension |
| 100/0.72 | Amorphous | 7.7 | White suspension |
| 100/0.74 | Amorphous | 7.7 | White suspension |
| 100/0.76 | Amorphous | 7.7 | White suspension |
| 100/0.78 | Amorphous | 7.7 | White suspension |

Lyophilisation and Reconstitution in Ringer's Lactate

Procedure:

Samples of 20 mg/mL: an aliquot of 2 mL was placed in the freezer for 2 hours. The samples were frozen using liquid nitrogen and the freeze-drying process was performed over 2 days (average vacuum ca. 0.05 mbar, temperature ca. −86° C.).

A white amorphous powder was obtained. The obtained solid was analysed by PXRD which confirmed the amorphous nature of the freeze-dried material. The obtained solid was solubilized with ca. 2 mL of Ringer's Lactate to a final concentration of 20 mg/mL and checked for precipitation and pH.

Samples of 100 mg/mL: an aliquot of 1.5 mL was placed in the freezer for 2 hours. The samples were frozen using liquid nitrogen and the freeze-drying process was performed over 2 days (average vacuum ca. 0.05 mbar, temperature ca. −86° C.).

A white amorphous powder was obtained. The obtained solid was analysed by PXRD which confirmed the amorphous nature of the freeze-dried material. The obtained solid was solubilized with ca. 7.5 mL of Ringer's Lactate to a final concentration of 100 mg/mL and checked for precipitation and pH

TABLE 31

Reconstitution in Ringer's Lactate solution (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 20/0.6 | Amorphous | 7.5 | Cloudy |
| 20/0.62 | Amorphous | 7.5 | Cloudy |
| 20/0.64 | Amorphous | 7.4 | Clear solution |
| 20/0.66 | Amorphous | 7.5 | Clear solution |
| 20/0.68 | Amorphous | 7.5 | Clear solution |
| 20/0.70 | Amorphous | 7.5 | Clear solution |
| 20/0.72 | Amorphous | 7.5 | Clear solution |
| 20/0.74 | Amorphous | 7.5 | Clear solution |
| 20/0.76 | Amorphous | 7.5 | Clear solution |
| 20/0.78 | Amorphous | 7.6 | Clear solution |

TABLE 32

Reconstitution in Ringer's Lactate solution (concentration of letermovir free base of 20 mg/ml).

| Letermovir Free Base concentration [mg/ml]/ NaOH/Letermovir Molar Ratio | PXRD | pH | Precipitation/ solubility |
|---|---|---|---|
| 100/0.6 | Amorphous | 7.5 | White suspension |
| 100/0.62 | Amorphous | 7.5 | White suspension |
| 100/0.64 | Amorphous | 7.4 | White suspension |
| 100/0.66 | Amorphous | 7.4 | White suspension |
| 100/0.68 | Amorphous | 7.4 | White suspension |
| 100/0.70 | Amorphous | 7.4 | White suspension |
| 100/0.72 | Amorphous | 7.4 | Clear solution |
| 100/0.74 | Amorphous | 7.4 | Clear solution |
| 100/0.76 | Amorphous | 7.4 | Clear solution |
| 100/0.78 | Amorphous | 7.5 | Clear solution |

The invention claimed is:

1. A pharmaceutical composition comprising letermovir of formula (I), and a source of sodium ions (I)

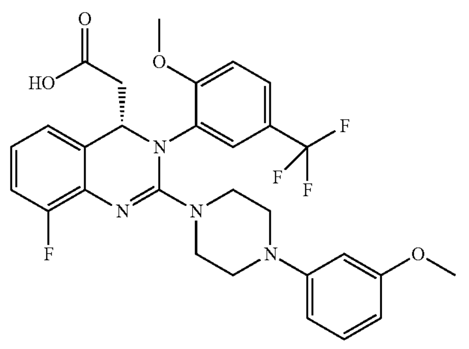

wherein the pharmaceutical composition
- comprises the sodium ions in a molar ratio to letermovir in the range of from 0.72 to 0.90:1.00; and
- exhibits a pH in the range of from 7 to 8 when said pharmaceutical composition is dissolved in water in a concentration range of from 20 to 100 mg/mL with respect to letermovir; and
- is essentially free from complexing solubilizing agents selected from the group consisting of PEG, lysine, arginine, and cyclodextrins.

2. The pharmaceutical composition according to claim 1, further comprising at least one excipient selected from the group consisting of carbohydrates, amino acids, polyalkoxy compounds, and polyvinylpyrrolidones.

3. The pharmaceutical composition according to claim 1, wherein the pharmaceutical composition is essentially free from complexing solubilizing agents.

4. The pharmaceutical composition according to claim 1, wherein the pharmaceutical composition further comprises a polyalkoxy compound, and is essentially free from other complexing solubilizing agents.

5. The pharmaceutical composition according to claim 2, wherein the excipient is mannitol, sucrose, or a combination thereof.

6. The pharmaceutical composition according to claim 2, further comprising at least one excipient selected from sucrose, mannitol, phenylalanine, poloxamer 188, and polyvinylpyrrolidone PF12.

7. The pharmaceutical composition according to claim 1, further comprising a buffer.

8. The pharmaceutical composition according to claim 1, wherein the pharmaceutical composition comprises the sodium ions in a molar ratio to letermovir in the range of from 0.80 to <1.00:1.00.

9. The pharmaceutical composition according to claim 1, wherein the pharmaceutical composition comprises the sodium ions in a molar ratio to letermovir in the range of from 0.80 to 0.90:1.00.

10. The pharmaceutical composition according to claim 1, wherein the pharmaceutical composition is capable of exhibiting a pH in the range of from 7.4 to 7.8, when said pharmaceutical composition is dissolved in water in a concentration range of from 20 to 100 mg/mL with respect to letermovir.

11. The pharmaceutical composition according to claim 1, further comprising a Tris hydroxy aminomethane (Tris).

12. A method for treatment of virus infections by members of the herpes viridae group comprising administering to an infected subject the pharmaceutical composition according to claim 1.

13. A method for prevention of virus infections by members of the herpes viridae group comprising administering to a subject the pharmaceutical composition according to claim 1.

14. A method for treatment of a human cytomegalovirus (HCMV) infection comprising administering to an infected subject the pharmaceutical composition according to claim 1.

15. A method for prevention of a human cytomegalovirus (HCMV) infection comprising administering to a subject the pharmaceutical composition according to claim 1.

16. A method of producing the pharmaceutical composition as defined in claim 1, comprising the following steps:
- i) providing a solution of letermovir and sodium ions, wherein the molar ratio of sodium ions to letermovir is in the range of from 0.72 to 0.90:1.00, and optionally at least one excipient selected from the group consisting of carbohydrates, amino acids, polyalkoxy compounds, and polyvinylpyrrolidones,
- ii) optionally adjusting the pH of the solution obtained in step i) to a range of from 7 to 8, and
- iii) optionally filtering said solution.

17. The method according to claim 16, further comprising freeze-drying the obtained solution to provide a lyophilizate.

18. The method according to claim 17, further comprising reconstituting the lyophilizate in a first parenterally acceptable diluent to provide a reconstituted solution containing letermovir at a concentration in the range of from 20 to 100 mg/mL, and optionally subsequently diluting said reconstituted solution with a second parenterally acceptable diluent to a final concentration which is acceptable for injection or infusion, wherein said first and said second parenterally acceptable diluents can be the same or different.

19. The method according to claim 16, wherein said at least one excipient is selected from sucrose, mannitol, phenylalanine, poloxamer 188, and polyvinylpyrrolidone PF12.

20. A pharmaceutical composition obtainable by the method as defined in claim 16.

21. A method for treatment of virus infections by members of the herpes viridae group comprising administering to an infected subject the pharmaceutical composition as defined in claim 20.

22. A method for prevention of virus infections by members of the herpes viridae group comprising administering to a subject the pharmaceutical composition as defined in claim 10.

23. A method for treatment of a human cytomegalovirus (HCMV) infection comprising administering to an infected subject the pharmaceutical composition as defined in claim 20.

24. A method for prevention of a human cytomegalovirus (HCMV) infection comprising administering to a subject the pharmaceutical composition as defined in claim 20.

* * * * *